(12) United States Patent
Cevc et al.

(10) Patent No.: US 7,867,480 B1
(45) Date of Patent: Jan. 11, 2011

(54) NON-INVASIVE VACCINATION THROUGH THE SKIN

(76) Inventors: Gregor Cevc, Tassilostrasse 3, 82/13/1, Gauting (DE); Amla Chopra, 924 Four Mile Rd. NW., Apt. 2D, Waluer, MI (US) 49544-1581

( * ) Notice: Subject to any disclaimer, the term of this patent is extended or adjusted under 35 U.S.C. 154(b) by 0 days.

(21) Appl. No.: 09/890,335

(22) PCT Filed: Jan. 26, 2000

(86) PCT No.: PCT/EP00/00597

§ 371 (c)(1),
(2), (4) Date: Apr. 8, 2002

(87) PCT Pub. No.: WO00/44349

PCT Pub. Date: Aug. 3, 2000

(30) Foreign Application Priority Data

Jan. 27, 1999 (EP) .................................. 99101479

(51) Int. Cl.
*A61K 9/113* (2006.01)
(52) U.S. Cl. .................................................. 424/85.1
(58) Field of Classification Search ................. None
See application file for complete search history.

(56) References Cited

U.S. PATENT DOCUMENTS

| | | |
|---|---|---|
| 4,036,953 A | 7/1977 | Adam |
| 4,095,596 A | 6/1978 | Grayson |
| 4,185,100 A | 1/1980 | Rovee |
| 4,369,182 A | 1/1983 | Ghyczy |
| 4,383,993 A | 5/1983 | Hussain et al. |
| 4,619,794 A | 10/1986 | Hauser et al. |
| 4,666,747 A | 5/1987 | Quinn |
| 4,731,210 A | 3/1988 | Weder |
| 4,746,509 A | 5/1988 | Haggiage et al. |
| 4,783,450 A | 11/1988 | Fawzi et al. |
| 4,849,224 A | 7/1989 | Chang et al. |
| 4,897,269 A | 1/1990 | Mezei |
| 4,911,928 A | 3/1990 | Wallach |
| 4,921,706 A | 5/1990 | Roberts |
| 4,937,078 A | 6/1990 | Mezei et al. |
| 4,937,254 A | 6/1990 | Sheffield |
| RE33,273 E | 7/1990 | Speaker |
| 4,938,970 A | 7/1990 | Hustead |
| 4,944,948 A | 7/1990 | Uster |
| 4,954,345 A | 9/1990 | Muller et al. |
| 4,983,395 A | 1/1991 | Chang et al. |
| 5,008,050 A | 4/1991 | Cullis |
| 5,043,165 A | 8/1991 | Radhakrishnan |
| 5,049,392 A | 9/1991 | Weiner |
| 5,104,661 A | 4/1992 | Lau |
| 5,145,684 A | 9/1992 | Liversidge et al. |
| 5,154,930 A | 10/1992 | Popescu et al. |
| 5,202,125 A | 4/1993 | Ebert et al. |
| 5,209,720 A | 5/1993 | Unger |
| 5,238,613 A | 8/1993 | Anderson |
| 5,244,678 A | 9/1993 | Legros et al. |
| 5,322,685 A | 6/1994 | Nakagawa |
| 5,460,820 A | 10/1995 | Ebert et al. |
| 5,498,418 A | 3/1996 | Beutner et al. |
| 5,498,420 A | 3/1996 | Edgar |
| 5,510,118 A | 4/1996 | Bosch et al. |
| 5,552,160 A | 9/1996 | Liversidge et al. |
| 5,585,109 A | 12/1996 | Hayward |
| 5,607,692 A | 3/1997 | Ribier et al. |
| 5,614,178 A | 3/1997 | Bloom et al. |
| 5,648,095 A | 7/1997 | Illum et al. |
| 5,653,987 A | 8/1997 | Modi |
| 5,654,337 A | 8/1997 | Roentsch et al. |
| 5,681,849 A | 10/1997 | Richter et al. |
| 5,716,526 A | 2/1998 | Keleman |
| 5,716,638 A | 2/1998 | Touitou et al. |
| 5,741,515 A | 4/1998 | Ciceri et al. |
| 5,763,422 A | 6/1998 | Lichtenberger |
| 5,783,208 A | 7/1998 | Venkateshwaran et al. |
| 5,783,210 A | 7/1998 | Tremblay |

(Continued)

FOREIGN PATENT DOCUMENTS

AU 1740283 7/1983

(Continued)

OTHER PUBLICATIONS

Paul, A., and G. Cevc. Vaccine Research, 4(3):145-164. 1995.*
Ellis (Chapter 29 of Vaccines, Plistkin, et al. (eds) WB Saunders, Philadelphia, 1998, pp. 568-574.*
Cevc, G. Drug delivery across the skin. Exp. Opin. Invest. Drugs (1997) 6: 1887- 1937.
Cevc, G., et al., Transfersomes, liposomes and other lipid suspensions on the skin: permeation enhancement, vesicle penetration, and transdermal drug delivery; Critical Reviews in Therapeutic Drug Carrier Systems, 13(3-4):257-388 (1996).
Cevc, G., et al., Ultraflexible Vesicles, Transfersomes, Have an Extremely Low Permeation Resistance and Transport Therapeutic Amounts of Insulin Across the Intact Mammalian Skin. Biochim. Biophys. Acta (1998) 1368: 201-21 5.).

(Continued)

*Primary Examiner*—Robert B Mondesi
*Assistant Examiner*—Brian J Gangle
(74) *Attorney, Agent, or Firm*—Neymeyer-Tynkov LLC; Valerie Neymeyer-Tynkov

(57) ABSTRACT

The present invention relates to novel vaccines for the non-invasive, transcutaneous administration of antigens associated with ultradeformable carriers, for the purpose of prophylactic or therapeutic vaccination. The vaccines comprise (a) a transdermal carrier which is a penetrant, (b) a compound which specifically releases or specifically induces cytokine or anticytokine activity or exerts such an activity itself, (c) an antigen, an allergen, a mixture of antigens and/or a mixture of allergens, and (d) a chemical irritant. The invention further relates to methods for the vaccination of mammals for obtaining a protective or therapeutic immune response.

39 Claims, 14 Drawing Sheets

U.S. PATENT DOCUMENTS

Figure 1:
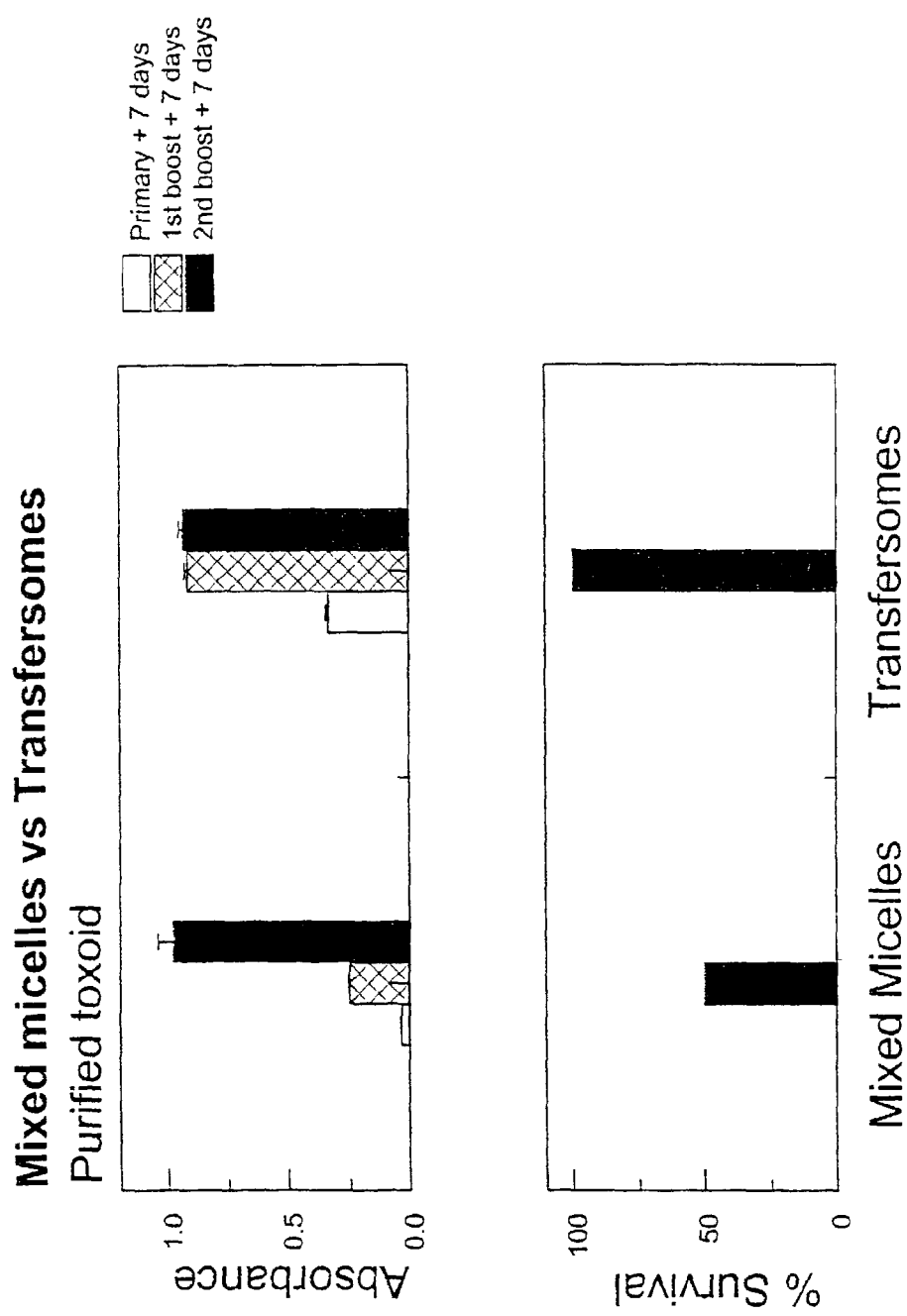

| | | | |
|---|---|---|---|
| 5,837,289 A | 11/1998 | Grasela | |
| 5,858,330 A | 1/1999 | Boltri et al. | |
| 5,874,095 A | 2/1999 | Deckner et al. | |
| 5,874,422 A | 2/1999 | Krause et al. | |
| 5,891,472 A | 4/1999 | Russell | |
| 5,958,379 A | 9/1999 | Regenold et al. | |
| 5,985,860 A | 11/1999 | Toppo | |
| 6,028,066 A | 2/2000 | Unger | |
| 6,045,827 A | 4/2000 | Russell | |
| 6,069,172 A | 5/2000 | Bertini et al. | |
| 6,083,996 A | 7/2000 | Buyuktimkin | |
| 6,165,500 A | 12/2000 | Cevc et al. | |
| 6,193,996 B1 | 2/2001 | Effing et al. | |
| 6,200,598 B1 | 3/2001 | Needham | |
| 6,214,386 B1 | 4/2001 | Santus et al. | |
| 6,248,329 B1 * | 6/2001 | Chandrashekar et al. | 424/191.1 |
| 6,248,353 B1 | 6/2001 | Singh | |
| 6,261,559 B1 | 7/2001 | Levitt | |
| 6,276,598 B1 | 8/2001 | Cheng | |
| 6,277,892 B1 | 8/2001 | Deckner et al. | |
| 6,294,192 B1 | 9/2001 | Patel et al. | |
| 6,303,141 B1 | 10/2001 | Fischer et al. | |
| 6,333,044 B1 | 12/2001 | Santus | |
| 6,387,383 B1 | 5/2002 | Dow et al. | |
| 6,448,296 B2 | 9/2002 | Yasueda et al. | |
| 6,451,339 B2 | 9/2002 | Patel et al. | |
| 6,517,864 B1 | 2/2003 | Jacobsen | |
| 6,562,370 B2 | 5/2003 | Luo et al. | |
| 6,577,880 B1 | 6/2003 | Ishida | |
| 6,582,724 B2 | 6/2003 | Hsu et al. | |
| 6,586,000 B2 | 7/2003 | Luo et al. | |
| 6,645,520 B2 | 11/2003 | Hsu et al. | |
| 6,645,529 B2 | 11/2003 | Gergely et al. | |
| 6,673,363 B2 | 1/2004 | Luo | |
| 6,726,598 B1 | 4/2004 | Jarvis et al. | |
| 6,726,925 B1 | 4/2004 | Needham | |
| 6,797,276 B1 | 9/2004 | Glenn | |
| 6,835,392 B2 | 12/2004 | Hsu et al. | |
| 6,868,686 B2 | 3/2005 | Ueda | |
| 7,063,859 B1 | 6/2006 | Kanios | |
| 7,175,850 B2 | 2/2007 | Cevc | |
| 7,387,788 B1 | 6/2008 | Carrara | |
| 7,459,171 B2 | 12/2008 | Cevc | |
| 7,473,432 B2 | 1/2009 | Cevc | |
| 7,591,949 B2 | 9/2009 | Cevc | |
| 2001/0012849 A1 | 8/2001 | Wechter | |
| 2002/0003179 A1 | 1/2002 | Verhoff et al. | |
| 2002/0012680 A1 | 1/2002 | Patel et al. | |
| 2002/0037877 A1 | 3/2002 | Singh | |
| 2002/0048596 A1 | 4/2002 | Cevc et al. | |
| 2002/0106345 A1 | 8/2002 | Uhrich et al. | |
| 2002/0119188 A1 | 8/2002 | Niemiec et al. | |
| 2002/0147238 A1 | 10/2002 | Jerussi et al. | |
| 2003/0099694 A1 | 5/2003 | Cevc et al. | |
| 2004/0071767 A1 | 4/2004 | Cevc | |
| 2004/0105881 A1 | 6/2004 | Cevc et al. | |
| 2005/0123897 A1 | 6/2005 | Cevc et al. | |
| 2007/0031483 A1 | 2/2007 | Cevc | |
| 2007/0042030 A1 | 2/2007 | Cevc | |
| 2007/0184114 A1 | 8/2007 | Cevc | |
| 2007/0243203 A1 | 10/2007 | Abrecht | |
| 2008/0095722 A1 | 4/2008 | Cevc | |
| 2008/0279815 A1 | 11/2008 | Cevc | |
| 2008/0311184 A1 | 12/2008 | Cevc | |
| 2009/0042989 A1 | 2/2009 | Cevc | |
| 2009/0060989 A1 | 3/2009 | Cevc | |
| 2009/0060990 A1 | 3/2009 | Cevc | |
| 2009/0155235 A1 | 6/2009 | Cevc | |

FOREIGN PATENT DOCUMENTS

| | | |
|---|---|---|
| AU | 724218 | 9/2000 |
| CA | 1143656 | 3/1983 |
| CA | 1289420 | 9/1991 |
| CA | 2067754 | 2/1992 |
| CA | 2 052 164 | 9/1992 |
| CA | 2160775 | 11/1994 |
| DE | 3016976 | 11/1980 |
| DE | 3713494 | 10/1987 |
| EP | 0088046 | 9/1983 |
| EP | 0 102 324 | 11/1984 |
| EP | 0152379 | 8/1985 |
| EP | 0224837 | 11/1986 |
| EP | 0211647 | 2/1987 |
| EP | 0 220 797 | 5/1987 |
| EP | 0280492 | 8/1988 |
| EP | 0 298 280 | 1/1989 |
| EP | 0393707 | 10/1990 |
| EP | 0355095 | 8/1993 |
| EP | 0582239 | 2/1994 |
| EP | 0674913 | 4/1995 |
| EP | 0 704 206 | 9/1995 |
| EP | 0 707 847 | 10/1995 |
| EP | 0382716 | 1/1998 |
| EP | 0995435 | 4/2000 |
| EP | 1 031 346 | 8/2000 |
| EP | 1031347 | 4/2002 |
| JP | 61-271204 | 12/1986 |
| JP | 4-210925 A | 8/1992 |
| JP | 5-502042 A | 4/1993 |
| JP | 6-183954 A | 7/1994 |
| JP | 6-507420 A | 8/1994 |
| JP | 07-324029 | 12/1995 |
| JP | 8-183742 A | 7/1996 |
| WO | 87/01938 | 4/1987 |
| WO | 88/07362 | 10/1988 |
| WO | WO-90/09385 | 8/1990 |
| WO | 90/09782 | 9/1990 |
| WO | 90/11065 | 10/1990 |
| WO | 91/01596 | 2/1991 |
| WO | WO 91/01146 | 2/1991 |
| WO | 91/04013 | 4/1991 |
| WO | WO-92/03122 | 3/1992 |
| WO | WO 92/04009 | 3/1992 |
| WO | 92/05771 | 4/1992 |
| WO | 92/22292 | 12/1992 |
| WO | 93/19736 | 10/1993 |
| WO | 93/19737 | 10/1993 |
| WO | 94/26257 | 11/1994 |
| WO | 95/09831 | 4/1995 |
| WO | 95/35095 | 12/1995 |
| WO | 96/04526 | 2/1996 |
| WO | 96/19205 | 6/1996 |
| WO | 96/29999 | 10/1996 |
| WO | 97/35573 | 10/1997 |
| WO | 98/05539 | 2/1998 |
| WO | 98/06750 | 2/1998 |
| WO | 98/07414 | 2/1998 |
| WO | WO-98/17255 | 4/1998 |
| WO | WO 98/20734 | 5/1998 |
| WO | WO 9820734 A1 * | 5/1998 |
| WO | 98/24407 | 6/1998 |
| WO | 98/30215 | 7/1998 |
| WO | 98/33483 | 8/1998 |
| WO | 99/22703 | 5/1999 |
| WO | 00/00597 | 1/2000 |
| WO | 00/12060 | 3/2000 |
| WO | 00/13684 | 3/2000 |
| WO | 00/25822 | 5/2000 |
| WO | WO-00/24377 | 5/2000 |

| | | |
|---|---|---|
| WO | WO 00 38653 | 7/2000 |
| WO | 00/44349 | 8/2000 |
| WO | 00/44350 | 8/2000 |
| WO | 00/50007 | 8/2000 |
| WO | 01/00247 | 1/2001 |
| WO | 01/01962 | 1/2001 |
| WO | 01/01963 | 1/2001 |
| WO | 01/12155 | 2/2001 |
| WO | 02/07767 | 1/2002 |
| WO | 02/11683 | 2/2002 |
| WO | 02/32398 | 4/2002 |
| WO | 02/058670 | 8/2002 |
| WO | 2004/032900 | 4/2004 |
| WO | 2005/063213 | 7/2005 |
| WO | 2006/050926 | 5/2006 |

OTHER PUBLICATIONS

Deng, H., et al., Sustainable cutaneous gene delivery, Nature Biotechnology (1997) 15: 1388-1390.
Fries, K.M., et al., Evidence of fibroblast heterogeneity and the role of fibroblast subpopulations in fibrosis. Clin. Immunol. Immunopathol. (1994) 72(3): 283-292.
Glenn, G.M., et al., Skin immunisation made possible by Cholera toxin, Nature, 391(6670):851 (Feb. 26, 1998).
Glenn, G.M., et al., Transcutaneous Immunization with Cholera toxin Protects Mice Against Lethal Mucosal Toxin Challenge. J. Immunol (1998) 161: 3211-3214.
Kondo, S., et al., Epidermal cytokines in allergic contact dermatitis. J. Am. Acad. Dermatol. (1995) 33: 786-800.
Lohoff, M., et al., The Th1/Th2 paradigm and experimental murine Leishmaniasis, Int. Arch. Allergy Immunol. (1998) 115:191 -202.
Luger, T. A., et al., The role of cytokines and neuroendocrine hormones in cutaneous immunity and inflammation. Allergy (1995) 50: 292-302.
Nasir, A., et al., Contact dermatitis. Clinical perspectives and basic mechanisms, Clin. Rev. Allergy and Immmunol. (1996) 14: 151-184.
Pastore, S., et al., Granulocyte macrophage colony stimulating factor is overproduced by keratinocytes in atopic dermatitis: Implications for sustained dendritic cell activation in the skin. J. Clin. Invest. (1997) 99: 3009-3017.
Paul, A., et al., Non-invasive administration of protein antigens. Transdermal immunisation with the bovine serum albumin in transfersomes, Vaccine Res. (1995) 4: 145-164.
Paul, A., et al., Transdermal immunisation with large proteins by means of ultradeformable drug carriers. Eur. J. Immunol. (1995) 25: 3521 -3524.
Schätzlein, A., et al., Non-uniform cellular packing of the stratum corneum and permeability barrier function of intact skin: a high-resolution confocal laser scanning microscopy study using highly deformable vesicles (Transfersomes), Br. J. Dermatol. (1998) 138: 583-592.
Strange, P., et al., Staphylococcal enterotoxin B applied on intact normal and intact atopic skin induces dermatoma, Arch. Dermatol. (1996) 132: 27-33.
Wang, L.F., et al., Epicutaneous exposure of protein antigen induces a predominant Th2-like response with IgE production in mice, J. Immunol. (1996) 156: 4079-4082.
Almeida et al., "Nasal DeliVery of Vaccines", J. Drug Targeting, 3:455-467 (1996).
Bagnasco, et al., "Absorption and Distribution Kinetics of the Major Parietaria Judaica Alerg n (Par j1) Administered by Noninjectable Routes in Healthy Human Beings", J. Allergy CLin. Immunol. 100:122-9 (1997).
Bibgeroglu, et al., "Treatment of Estrogen-Dependent Gynecological Disorders with the Gonadotropin Releasing Hormone Agonist Buserelin", Gynecol. Endocrinol. 5:109-22 (1991).
Bruins et al, "Effect of Acute and Chronic Treatment with Desglycinamide [Arg8] Vasopressin in Young Male and Female Volunteers", Peptides 16:179-86 (1995).
Draghia et al., "Gene Delivery into the Central Nervous System by Nasal Instillation in Rats", Gene-Ther. 2:418-23 (1995).

Drejer et al, "Intranasal Administration of Insulin with Phospholipid as Absorption Enhancer: Pharmacokinetics in Normal Subjects", Diab. Med. 9:335-340 (1992).
Flanagan et al, "A Recombinant Human Adenovirus Expressing the Simian Immunodeficiency Virus Gag Antigen can Induce Long-Lived Immune Responses in Mice", J. Gen. Virol. 78:991-7 (1997).
Gizurarson et al., "Intranasal Administration of Insulin to Humans", Diabets Res. Clin. Pract. 12:71-84 (1991).
U.S. Appl. No. 09/890,371, filed Jul. 26, 2001, Cevc et al.
Ghigo et al., "Short Term Administration of Intranasal or Oral Hexarelin, a synthetic Hexapeptide, Does Not Desensitize the Growth Hormone Responsiveness in Human Aging", Eur. J. Endocrinol. 135:407-102 (1996).
Harris, A. S. "Review: Clinical Opportunities Provided by the Nasal Administration of Peptides", J. Drug Target. 1:101-16 (1993).
Huneycutt et al., "Distribution of Vesicular Stomatitis Virus Proteins in the Brains of BALB/c Mice Following Intranasal Inoculation: An Immunohistochemical Analysis", Brain Res. 635:81-95 (1994).
Hussain et al., "Does Increasing the Lipophilicity of Peptides Enhance Their Nasal ABsorpotion?", J. PHarm. Sci. 80:1180-1 (1991).
Ichikawa et al., "Anti-Osteopenic Effect of Nasal Salmon Calcitonin in Type I Osteoporotic Rats: Comparison with Subcutaneous Dosing", Biol. Pharm. Bull. 17:911-13 (1994).
Ilum, L., "The Nasal Delivery of Peptides and Proteins", Trends. Biotechnol. 9:284-9 (1991).
Iilum et al., "Intranasal Insulin", Clinical Pharmacokinet. 23:30-41 (1992).
Invetti et al., "Effect of Chronic Treatment with Octreotide Nasal Powder on Serum Levels of Growth Hormone, Insulin-like Growth Factor I, Insulin-like Growth Factor Binding Proteins 1 and 3 in Acromegalic Patients", J. Endocrinol. Invest. 19:548-55 (1996).
Kida et al., "CSF Drains Directly from the Subarachnoid Spce into Nasal Lyumphatics in the Rat. Anatomy, Histology and Immunological Significance", Neuropathol. Appl. Neurobiol. 19:480-448 (1993).
Laursen et al., "Bioavailability and Bioactivity of Three Different Doses of Nasal Growth Hormone (GH) Administered to GH-Deficient Patients:Comparison with Intravenous and Subcutaneous Administration", Eur. J. Endocrinol. 135:309-15 (1996).
Machida et al, "Absorption of Recombinant Human Granulocyte Colony-Stimulating Factor (rhG-CSF) from Rat Nasal Mucosa", Pharm. Res. 10(9)1372-7 (1993).
Maejima et al., "Comparison of the Effects of Various Fine Particles on IgE Antibody Production in Mice Inhaling Japanese Cedar Pollen Allergens", J. Toxicol. Environ. Health. 52:231-48 (1997).
Maitani et al., "Influence of Molecular Weight and Charge on Nasal Absorption of Dextran and DEAE-dextran in Rabbits", Intl. J. Pharmaceut. 49:23-27 (1989).
McMartin et al., "Analysis of Structural Requirements for the Absorption of Drugs and Macromolecules from the Nasal Cavity", J. Pharm. Sce. 76:535-540 (1987).
Mori et al., "Temperature- SEnstivie Parainfluenza Type 1 Vaccine Virus Directly Accesses the Central Nervous System by Infecting Olfactory Neurons", J. Gen. VIrol. 77:2121-4 (1996).
Naumann et al., "Vasopressin and Cognitive Processes: Two Event-Related Potential Studies", peptides 12:1379-84 (1991).
Pasechnik et al., "Macromolecular Drug Delivery to the CNS with Protein Carriers", Exp. Opin. Invest. Drugs 5:1255-1276 (1996).
Perras et al., "Sleep and Signs of Attention During 3 Months of Intranasal Vasoppresin: A Pilot Study in Two Elderly Subjects", peptides 17:1253-55 (1996).
Pietrowsky et al., "Brain Potential Changes after Intranasal vs. Intravenous Administration of Vasopressin: Evidence for a Direct Nose-Brain Pathway for Peptide Effects in Humans", Biol. Psychiatry 39:332-40 (1996).
Pihoker et al., "Diagnostic Studies with Intravenous and Intranasal Growth Hormone-Releasing Peptide-2 in Children of Short Stature", J. Clin. Endocrinol. Metab. 80(10):2987-92 (1995).
Pohl et al., "Modulation of Pain Perception in Man by a Vasopressin Analogue", Peptides 17:641-7 (1996).
Sarkar, M. "Drug Metabolism in the Nasal Mucosa", Pharm-Res. 9:1-9 (1992).

Shimoda et al., "Effects of Dose, PH and Osmolarity on Intranasal Absorption of Recombinant Human Erythropoietin in Rats", Biol. Pharm. Bull. 18(5):734-9 (1995).

Sperber et al., "Otologic Effects of Interferon Beta Serine in Experimental Rhinovirus Colds", Arch. Otolaryngol. Head. Neck. Surg. 118:933-6 (1992).

Ting et al., "Microparticles of Polyvinyl Alcohol for Nsal Delivery. I. Generation by Spray-Drying and Spray-Desolvation", Pharm. Res. 9:1330-5 (1992).

Tsume, et al., "Quantitative Evaluation of the Gastrointestinal Absorption of Protein into the Blood and Lymph Circulation", Biol. Pharm. Bull. 19(10) 1332-1337 (1996).

Watanabe, et al., "Absorption of Recombinant Human Granulocyte Colony-Stimulating Factor (rhG-CSF) and Blood Leukocyte Dynamics Following Intranasal Administration in Rabbits", Biol. Pharm. Bull. 16:93-95 (1993).

Watanabe et al., "Pharmacolinetics and Pharmacodynamics of Recombinant Human Granulocyte Colony-Stimulating Factor (rhG-CSF) following Intranasal Administration in Rabbits", J. Drug Target 3:231-38 (1995).

Wstenberg et al., "Pharmacokinetics of DGAVP in Plasma Following Intranasal and Oral Administration to Healthy Subjects". Peptides 15:1101-4 (1994).

Van Der Wiel, et al. Intranasal Calcitonin Suppresses Increased Bone Resorption During Short-Term Immobilization: A Double-Blind Study of the Effects of Intranasal Calcitonin on Biochemical Parameters of Bone Turnover:, J. Bone Mineral Res. 8:1459-65 (1993).

Office Action and Notice of References Cited issued in pending U.S. Appl. No. 09/890,371 on Oct. 27, 2009.

Claims pending in U.S. Appl. No. 09/890,371 as of Oct. 27, 2009.

Luger and Schwartz, "The role of cytokines and neuroendocrine hormones in cutaneous immunity and inflammation" Allergy 50:292-302 (1995).

Office Action (Restriction Requirement) issued Sep. 18, 2009 and Notice of Abandonment issued Apr. 15, 2010 in U.S. Appl. No. 11/638,091, abandoned, and a claims pending at the time of issuance of the Action.

Office Actions issued Nov. 18, 2009 and Jul. 23, 2008, in pending U.S. Appl. No. 09/284,683; along with claims pending when the Actions were issued and a Notice of References Cited issued with the Nov. 18, 2009 Action.

Office Action and Notice of References Cited issued Jul. 13, 2009 with claims pending when Action issued in pending U.S. Appl. No. 11/667,325.

Office Action and Notice of References Cited issued Feb. 18, 2010 with claims pending when Action issued in pending U.S. Appl. No. 10/357,618.

Cevc, "Transfersomes-mediated transepidermal delivery improves the regio-specificity and biological activity of corticosteroids in vivo" J. Controlled Release 45:211-226 (1997).

Holum, Elements of General and Biological Chemistry: John Wiley & Sons, USA (1987), pp. 324, 325.

Stryer, Biochemistry: W.H. Freeman & Co., San Francisco, California, USA (1981), pp. 208, 209.

Mathews & van Holde, Biochemistry: The Benjamin/Cummings Publishing Co., Redwood City, California (1990), pp. 303, 304.

Agerholm, C., et al., "Epithelial transport and bioavailability of intranasally administered human growth hormone formulated with the absorption enhancer didecanoyl-L-a-phosphatidylcholine and a-cyclodextrin in rabbits." J. Pharm. Sci. 83(12): 1706-11 (Dec. 1994).

Aungst et al, "Enhancement of naloxone penetration through human skin in vitro using fatty acids, fatty alcohols, surfactants, sulfoxides and amides," on International Journal of Pharmaceutics 33:225-234 (1986).

Berger, M. "Oral insulin 1922-1992: The history of continuous ambition and failure" Heinrich-Heine-University, Dusseldorf, Germany, pp. 144-148.

Beyer, C. et al., "Micro Emulsions" Pharmazie in unserer Zeit, No. 2 (1983), pp. 55-60.

Blume et al, "Drug-carrier and stability properties of the long-lived lipid vesicles: cryptosomes, in vitro and in vivo" J. Liposome Research 2(3):355-368 (1992).

Brendzel, A. et al., "Effects of lipid-soluble substances on the thermotropic properties of liposome filtration" Biochimica et Biophysica Acta, 601:260-270 (1980).

Burnette, R. et al., "Characterization of the Permselective Properties of Excised Human Skin During Iontophoresis," J. Pharmaceutical Sciences 76(10):765-773 (Oct. 1987).

Byas-Smith et al., "Transdermal clonidine compared to placebo in painful diabetic neuropathy using two stage 'enriched enrollment' design," Pain 60:267-274 (1995).

Calpena, et al., "Influence of the Formulation on the In Vitro Transdermal Penetration of Sodium Diclofenac" Arzneim-Forsch/Drug Res 49(II):1012-1017 (1999).

Carafa M., et al., "Lidocaine-loaded non-ionic surfactant vesicles: characterization and in vitro permeation studies" International J. of Pharmaceutics 231:21-32 (2002).

Castillo et al., "Glucocorticoids prolong rat sciatic nerve blockade in vivo from bupivacaine microspheres," Anesthesiology 85(5):1157-66 (1996).

Cevc, et al., "Phospholipids handbook", Marcel Dekker, Inc., New York, Basel, Hong Kong, Chaps. 11, 12 pp. 351-454; including pp. 375-376 and 404 (1993).

Cevc, et al., "Transdermal drug carriers: basic properties, optimization and transfer efficiency in the case of epicutaneously applied peptides," J. Contr. Rel. 36:3-16 (1995).

Cevc, G. et al., "New, highly efficient formulation of diclofenac for the topical, transdermal administration in ultradeformable drug carriers, transfersomes," Biochimica et Biophysica Acta 1514:191-205 (2001).

Cevc, G. et al., "The skin: a pathway for systemic treatment with patches and lipid-based agent carriers" Advanced Drug Delivery Reviews 18:349-378 (1996).

Cevc, G. et al., "Material Transport Across Permeability Barriers by Means of Lipid Vesicles", Handbook of Biological Physics, vol. 1, pp. 465-490 (1995).

Claims (pending as of about Aug. 8, 2007) filed Feb. 9, 2007 in U.S. Appl. No. 09/555,986.

Claims (pending as of about Aug. 8, 2007) filed May 8, 2007 in U.S. Appl. No. 11/667,325.

Claims (pending as of about Aug. 8, 2007) filed Feb. 26, 2007 in U.S. Appl. No. 10/984,450 (US 2005/0123897).

Claims (pending as of about Aug. 8, 2007) filed Jan. 22, 2007 in U.S. Appl. No. 10/037,480 (US 2003/0099694).

Claims (pending as of about Aug. 8, 2007) filed Jul. 12, 2007 in U.S. Appl. No. 09/284,683 (US 2002/0048596).

Claims (pending as of about Aug. 8, 2407) filed Jun. 20, 2007 in U.S. Appl. No. 10/357,618 (US 2005/0105881).

Claims (pending as of about Aug. 8, 2007) filed Oct. 11, 2006 in U.S. Appl. No. 11/545,904 (US 2007/0031483).

Claims (pending as of about Aug. 8, 2007) filed Oct. 20, 2006 in U.S. Appl. No. 10/357,617 (US 2004/0071767).

Clark, J.M., Jr. "Experimental Biochemistry," Biochemistry Division, Department of Chemistry, University of Illinois, pp. 47-48.

International Search Report for International Patent Application No. PCT/EP2005/011986 (Jul. 4, 2006).

Definition of Microbicide, Wikipedia, The Free Online encyclopedia (2007).

Edwards, et al., "Effects of Triton X-100 on Sonicated Lecithin Vesicles," Langmuir 5:473-478 (1989).

Fieser, L.F. et al, "Organische Chemie," Hans Ruprecht Hensel, 2nd revised edition, Verlag Chemie GmbH, Weinheim/Bergstr. p. 1250 (1968).

Fluka Chemica-BioChemica, Katalog 16, pp. 204, 830 (1988/1989).

Foldvari, "Effect of vehicle on topical liposomal drug delivery: petrolatum bases," J. Microencapsulation, 13(5):589-600 (1996).

Foldvari, "In vitro cutaneous and percutaneous delivery and in vivo efficacy of tetracaine from liposomal and conventionl vehicles," Pharmaceutical Research 11(11):1593-98 (1994).

Foldvari, et al., "Dermal drug delivery by liposome encapsulation: clinical and electron microscopic studies," J. Microencapsulation 7(4):479-489 (1990).

Frantzen et al., "Assessing the accuracy of routine photon correlation spectroscopy analysis of heterogeneous size distributions," AAPS PharmSciTech 4(3), Article 36:1-9 (2003).

Friedrich, I. et al., "Physicochemical characterization of a reverse micellar solution after loading with different drugs," Pharmazie 55(2000) 10, 755-758.

Gesztes, A. et al., "Topical Anesthesia of the Skin by liposome-encapsulated tetracaine," Anesth. Analg 67:1079-1081 (1988).

Golden et al., "Role of stratum corneum lipid fluidity transdermal drug flux," on J. of Pharmaceutical Sciences, American Pharmaceuticals Association 76(1):25-28 (Jan. 1987).

Grahame R., "Transdermal non-steroidal anti-inflammatory agents," BJCP 49(1):33-35 (Jan.-Feb. 1995).

Green et al., "In vitro and in vivo enhancement of skin permeation with oleic and lauric acids," on International Journal of Pharmaceuticals 48:103-111 (1988).

Helenius, et al., "Solubilization of membranes by detergents," BBA 415:29-79 (1975).

Henmi, T. et al., "Application of an oily gel formed by hydrogenated soybean phospholipids as a percutaneous absorption-type ointment base," Chem. Pharm. Bull. 42(3) 651-655 (1994).

Ito, Yoshimasa et al., "Percutaneous absorption of acemetacin from a membrane controlled transdermal system and predicition of the disposition of the drug in rats," Biol. Pharm. Bull. 16(6):583-88 (1993).

Office Actions and Interview Summary issued Dec. 11 & Apr. 3, 2008, Oct. 10 & Jan. 29, 2007, Jul. 26 & May 19, 2006 in U.S. Appl. No. 09/890,371, currently pending.

Claims pending on Dec. 11, 2008 and currently pending claims in U.S. Appl. No. 09/890,371.

Office Actions and Notices of Allowability issued on Jan. 3, 2006, Mar. 2, 2005, Jul. 2, 2001 in U.S. Appl. No. 09/621,574, abandoned.

Claims pending on Jan. 3, 2006 in U.S. Appl. No. 09/621,574.

Office Actions and Notices of Allowability issued on May 25, 1999, Jun. 24, 1998 and Dec. 19, 1997 in U.S. Appl. No. 07/844,664, granted as US Pat. 6,165,500.

Bibliographic page and claims granted in US Pat. 6,165,500, 2000.

Office Action issued on Mar. 27, 2007 in U.S. Appl. No. 11/481,804, abandoned.

Claims pending on Mar. 27, 2007 in U.S. Appl. No. 11/481,804.

Office Actions issued Aug. 10, 2006; Dec. 21 & Apr. 1, 2005; Mar. 23, 2004; May 20 & Jan. 9 (Advisory), 2003; Jun. 24, 2002; Sep. 25, 2001 in U.S. Appl. No. 09/555,986, abandoned.

Claims pending on Aug. 10, 2006 in U.S. Appl. No. 09/555,986.

Office Actions issued Nov. 25, 2008, Apr. 2, 2008, Nov. 29, 2007, Aug. 17, 2007, Mar. 12, 2007, Jul. 10, 2006 in U.S. Appl. No. 09/284,683, currently pending.

Office Actions issued Nov. 4, 2005, Apr. 15, 2005, Jun. 24, 2004, Mar. 18, 2004 (Advisory) in U.S. Appl. No. 09/284,683, currently pending.

Office Actions issued Oct. 7, 2003, Jun. 18, 2003 (Advisory), Jan. 3, 2003, Apr. 10, 2002, Jul. 6, 2001 (Advisory), Apr. 20, 2001, Aug. 22, 2000 in U.S. Appl. No. 09/284,683, currently pending.

Claims pending on Nov. 25, 2008 in U.S. Appl. No. 09/284,683.

Office Actions issued Dec. 30 and Nov. 28, 2008 in U.S. Appl. No. 11/667,325, currently pending.

Claims pending on Dec. 30, 2008 in U.S. Appl. No. 11/667,325.

Office Actions issued on May 26, 2009; Oct. 28 & Mar. 19, 2008; Aug. 2, 2007; and Dec. 28, 2006 in U.S. Appl. No. 10/357,618, currently pending.

Claims pending on May 26, 2009 in U.S. Appl. No. 10/357,618.

Office Actions & Notices of Allowability issued Oct. 16, 2008, Sep. 21 & Jan. 19, 2007, & May 30, 2006 in U.S. Appl. No. 10/357,617, granted as US Patent No. 7,473,432.

Bibliographic page and granted claims of US Patent No. 7,473,432, 2009.

Office Actions and Notice of Allowance issued on May 29, 2009, May 16, 2007, Aug. 28, 2006 and Feb. 7, 2006 in U.S. Appl. No. 10/984,450, allowed.

Claims pending on May 29, 2009 in U.S. Appl. No. 10/984,450.

Office Actions, Notices of Allowability issued Aug. 21 & Jan. 9, 2008, Apr. 11, 2007, Nov. 20, 2006, Dec. 19 & Mar. 30, 2005, Apr. 21, 2004 Oct. 16, 2003 in U.S. Appl. No. 10/037,480, granted as US Patent 7,459,171.

Bibliographic page and granted claims of US Patent No. 7,459,171, 2008.

Office Actions issued Oct. 19, 2005, Feb. 2, 2005, May 27, 2004 (Advisory), Nov. 4, 2003, Jun. 17, 2003, Nov. 29, 2002, in U.S. Appl. No. 09/887,493, granted (US 7,175,850).

Notice of Allowability dated Sep. 12, 2006 in U.S. Appl. No. 09/887,493, and bibliographic page and granted claims of US Patent No. 7,175,850.

Office Action issued Oct. 23, 2008 in U.S. Appl. No. 11/638,091, currently pending.

Claims pending on Oct. 23, 2008 in U.S. Appl. No. 11/638,091.

International Search Report issued in counterpart PCT Application No. PCT/EP00/00597 (published as WO 00/44349), 2000.

International Preliminary Examination Report issued in counterpart PCT Application No. PCT/EP00/00597 (published as WO 00/44349), 2000.

Partial European Search Report issued in counterpart European Appln. No. 991014879.6 (granted as EPO Patent No. 1 031 346 B1), 2000.

Examination Reports issued in counterpart European Appln. No. 99101479.6 (granted as EPO Patent No. 1 031 346 B1), 2000.

Bibliographic page and English language claims of granted counterpart EPO Patent No. 1 031 346 B1 (counterpart European Appln. No. 99101479), 1999.

"Itching" (2006) From Merck Manual Home Edition Online: www.merck.com/mmhe/pring/sec18/ch203/ch203b.html.

Paul et al., "Transdermal immunisation with an integral membrane component, gap junction protein . . . " Vaccine 16(2-3):188-195 (1998).

Karzel and R.K. Liedtke, "Mechanism Transkutaner Resorption," on Grundlagen/Basics, pp. 1487-1491.

Katoulis et al., "Efficacy of a new needleless insulin delivery system monitoring of blood glucose fluctuations and free insulin levels," on International J. of Artificial Organs 12(5):333-338 (1989).

Klibanov, et al., "Activity of amphipathic poly(ethylene gycol) 5000 to prolong the circulation time of liposomes depends on the liposome size and is unfavorable for immunoliposome binding to target," BBA 1062:142-148 (1991).

Knepp et al., "Controlled drug release from a novel liposomal delivery system II. Transdermal delivery characteristics," J. Contr. Release 12(1):25-30 (Mar. 1990) Amsterdam, NL.

Lasch, J. et al., "Interactions of external lipids (lipid vesicles) with the skin" J. Liposome Research 5(3):543-569 (1995).

Lehmann, J. et al., "Analgesic and anti-inflammatory efficacy of IDEA-070 in UVB-induced sunburn." J. Eur. Acad. Dermatol. Venereol. 18(S2):267-268 (Oct. 2004).

Litchenberg, D. et al., "Solubilization of phospholipids by detergents: structural and kinetic aspects" BBA 737:285-304 (1983).

Lobbecke, et al., "Effects of short-chain alcohols on the phase behavior and interdigitation of phosphatidylcholine bilayer membranes" BBA 1237:59-69 (1995).

Mayer, L.D. et al., "Vesicles of variable sizes produced by a rapid extrusion procedure," BBA 858:161-168 (1986).

Merck Index: 10th Edition. 1983. pp. 779-780.

Mezei, "Liposomes as a skin drug delivery system," 1985 Elsevier Science Publishers B.V. (Biomedical Division) pp. 345-358.

Ogiso, Taro et al., "Membrane-controlled transdermal therapeutic system containing clonazepam and anticonvulsant activity after its application." Chem. Pharm. Bull. 37(2):446-449 (1989).

Patel, H.M. et al., "Oral administration of insulin by encapsulation within liposomes," FEBS Letters 62(1):60-63 (Feb. 1976).

Patel, H.M., "Liposomes as a controlled-release system," Biomedical Society Transactions 609th Meeting, Leeds, pp. 513-516.

Peters, et al., "Pharmacodynamics of a liposomal preparation for local anaeshesia," Arzneim-Forsch/Drug Res. 45(II), Nr12 (1995), pp. 1253-1256.

Planas, et al., "Noninvasive percutaneous induction of topical analgesia by a new type of drug carrier, and prolongation of local pain insensitivity by anesthetic liposomes," Anesth. Analg. 75:615-621 (1992).

Price, C.E., "A review of the factors influencing the penetration of pesticides through plant leaves," on I.C.I. Ltd., Plant Protection Division, Jealott's Hill Research Station, Bracknell, Berkshire RG12 6EY, U.K., pp. 237-252.

Product Information; "Polysorbate 80 VG" (2004).

Product Information: "Tween 80 Pure" (2004).
Prof. Dr. K-U Benner, Der Korper des Menschen, "The human body" Weltbild GmbH Augsburg Chapter 4 p. 49 (1995).
Ranade V., "Drug delivery systems. 6. Transdermal drug delivery," J. Clin. Pharmacol. 31:401-418 (1991).
Roeding, J. "Liposomes and niosomes in pharmacy and cosmetics state of art prospects, techniques of visualizing vesicular systems, interaction of liposomes with the skin" Training course No. 105 from May 14-16, 1990. Maritim Hotel Nurnberg, Frauentorgraben 11, 8500, Nurnberg.
Schramlova, J. et al., "The effect of an antiphlogisitic incorporated in liposomes on experimentally induced inflammation," Fola Biologica (Praha) 43:195-199 (1997).
Schreier, H. "Liposomes—A novel drug carrier. I. Phospholipids; production and characterization of liposomes; II. Destiny of liposomes in vivo; use in therapy," Pharmazie in unserer Zeit, No. 4 (1982).
SERVA Feinbiochyemica, Katalog, pp. 201-202 (1986/1987).
Siddiqui, O. et al., "Nonparenteral administration of peptide and protein drugs," CRC Critical Review in Therapeutic Drug Carrier Systems, vol. 3, Issue 3 p. 195-208.
Stoye, I. et al., "Transformation of a liposomal dispersion containing ibuprofen lysinate and phospholipids into mixed micelles—physicochemical characterization and influence on drug permeation through excised human stratum corneum," Eur. J. Pharmaceuticals and Biopharmaceuticals 46:191-200 (1998).
Swenson, E. Scott and William J. Curatolo, "Intestinal permeability enhancement for proteins, peptides and other polar drugs: mechanisms and potential toxicity" Advanced Drug Delivery Reviews, 8:39-92 (1992).
Trotta, M. et al., "Deformable liposomes for dermal administration of methotrexate," International J. of Pharmaceutics (Kidlington) 270(1-2) Feb. 11, 2004, pp. 119-125.
Trotta, M. et al., "Elastic liposomes for skin delivery of dipotassium glycyrrhizinate," International J. of Pharmaceutics (Kidlington) 241(2) Jul. 25, 2002, pp. 319-327.
Valenta, C. et al, "Evaluation of novel soya-lecithin formulations for dermal use containing ketoprofen as a model drug," J. Contr. Release 63:165-173 (2000).
Vinggaard, A.M., et al., "Didecanoyl phosphatidylcholine is a superior substrate for assaying mammalian phospholipase D." Biochem. J. 319:861-864 (1996).
Vinson, P. et al., "Vesicle-micelle transition of phosphatidylcholine bilayers and octylglucoside elucidated by cryo-transmission electron microscopy," Biophys. J., Biophysical Society vol. 56, Oct. 1989 pp. 669-681.
Vyas et al., "Liposomally encapsulated diclofenac for sonophoresis induced systemic delivery," J. Microencapsulation, 1995, 12(2):149-154.
Wearley LL, "Recent progress in protein and peptide delivery by noninvasive routes." Crit. Rev. Ther. Drug Carrier Syst. 8:331-94 (1991).

Wess, L.: "All in the Family." Biocentury, the Bernstein Report on Biobusiness, 12(22):A11-A12 May 17, 2004.
Yuan, et al., "Cationic liposome and gene transfer," Progress in Physiological Science, 28(2): 163-165 (1997) (English translation only).
Jackson, M.L. et al., "Solubilization of phosphatidylcholine bilayers by octyl glucoside" Biochemistry 21:4576-4582 (1982).
English language abstract of EP 0 298 280 A from Derwent.
English language abstract of EP 0 102 324 from Derwent.
Pierson et al., "Synthesis and biological evaluation of potent, selective, hexapeptide CCK-A agonist anorectic agents" J. Med. Chem. 40:4302-07 (1997).
Lee et al., "Intranasal bioavailability of insulin powder formulations: Effect of permeation enhancer-to-protein ratio" J. Pharm. Sci. 80(8):725-29 (1991).
Shao et al., "Cyclodextrins as nasal absorption promoters of insulin: Mechanistic evaluations" Pharm. Res. 9 (9):1157-63 (1992).
Illum et al., "Chitosan as a novel nasal delivery system for peptide drugs" Pharm. Res. 11(8):1186-89 (1994).
Lowell et al., "Proteosomes, emulsomes, and cholera toxin B improve nasal immunogenicity of human immunodeficiency virus gp160 in mice: Induction of serum, intestinal, vaginal, and lung IgA and IgG" J. Infect. Dis. 175:292-301 (1997).
Schreier et al., "Liposomen—ein neuartiger Arzneist offtrager II. Schicksal von Liposomen in vivo: Einsatz in der Therapie", Pharmazie in unserer Zeit No. 4 (1982), pp. 103-108.
English Translation/Summary—Beyer C. et al. "Microemulsions" Pharmazie in unserer zeit, No. 2 (1983).
English Translation/Summary—Fieser, L.F. et al.,"Organishe Chemie" Hans Ruprecht Hensel, 2nd revised edition, Verlag Chemie GmbH, Weinheim/Bergstr. p. 1250 (1968).
English Translation/Summary—Roeding, J. "Liposomes and niosomes in pharmacy and cosmetics: state of art prospects, techniques of visualizing vesicular systems, interaction of liposomes with the skin" Training course No. 105 from May 14-16, 1990, Maritim Hotel Nurnberg, Frauentrgraben 11, 8500, Nurnberg.
English Translation/Summary—Schreier H., "Liposomes—A novel drug carrier I. Phospholipids production; II. Destiny of liposomes in vivo; use in therapy" Pharmazie in unserer Zeit, No. 4 (1982).
Office Action issued Jun. 17, 2010 with claims pending when Action issued in pending U.S. Appl. No. 11/545,904.
Information Disclosure Statements submitted in U.S. Appl. No. 09/890,371.
Holzbach RT, "Detection of vesicles in native and model biles by morphological and other structural techniques: applications and limitations" Hepatology Sep. 12 (3 Pt 2) pp. 106S-112S (1990).
English version of claims pending in copending U.S. Appl. No. 09/890,371's counterpart Japanese application as of date of issuance of Japanese Office Action.
Y. Aramaki et al., "Activation of systemic and mucosal immune response following nasal administration of liposomes", Vaccine 12(13):1241-45(1994).

* cited by examiner

Immunomodulant effect, for example cytokines
*Impure toxoid*

Figure 9

Serum was collected for the assay on 7th day after 2nd boost
No protection was observed in any of the groups

Adjuvant effect: for example Heat Labile Toxin (HLT) from E.coli

Figure 11

Bi-Valent Vaccines: Anti-Tetanus and anti-Cholera response to the administration of both antigens together in Transfersomes on the skin

NON-INVASIVE VACCINATION THROUGH THE SKIN

CROSS-REFERENCE TO RELATED APPLICATIONS

This application is a national stage entry of PCT Application No. PCT/EP00/00597, filed Jan. 26, 2000, which claims priority from European Patent Application No. EP 99101479, filed Jan. 27, 1999.

The present invention relates to novel vaccines for the non-invasive, transcutaneous administration of antigens associated with ultradeformable carriers, for the purpose of prophylactic or therapeutic vaccination. The vaccines comprise (a) a transdermal carrier which is a penetrant, suspended in or dispersed in an aqueous solvent in the form of a minute fluid droplet surrounded by a membrane-like coating of one or several layers of at least two different substances or two different forms of a substance with the tendency to aggregate, said substances or forms of a substance differing by at least the factor of 10 in solubility in a preferably aqueous, liquid medium, such that the average diameter of homo-aggregates of the more soluble substance or form of the substance or the average diameter of the hetero-aggregates consisting of both said substances or forms of said substance is smaller than the average diameter of homo-aggregates of the less soluble substance or form of the substance, and/or wherein the more soluble component tends to solubilise the penetrating droplet and wherein the content of such component amounts to up to 99 mol-% of the concentration required to solubilise the droplet or else corresponds to up to 99 mol-% of the saturating concentration in the un-solubilised droplet, whichever is higher, and/or wherein the elastic deformation energy of the droplet surrounding the membrane-like coating is at least 5×, more preferably is at least 10× lower and ideally is more than 10× lower than that of the red blood cells or of the phospholipid bilayers with fluid aliphatic chains, (b) a compound which specifically releases or specifically induces cytokine or anti-cytokine activity or exerts such an activity itself, and (c) an antigen or an allergen. The invention further relates to methods for corresponding therapeutic or prophylactic vaccination of mammals.

Several documents are cited throughout the text of this specification. Each of the documents cited herein (including any manufacturer's specifications, instructions, etc.) are hereby incorporated by reference; however, there is no admission that any document cited is indeed prior art of the present invention. Further incorporated by reference is the complete disclosure content of the co-pending application filed in the name of IDEA AG and bearing the title "Transnasal transport/immunization with highly adaptable carriers" (U.S. application Ser. No. 09/890,371, published as WO 2000/044350).

Skin is the best accessible, but also the most difficult, entry into the body, due to the presence of the stratum corneum. This horny layer of the skin is an evolutionary optimized barrier which resembles the blood vessel wall, in that it comprises flaccid, tightly packed and laterally overlapping cells, whereby the basic cellular-tile motif in the stratum corneum is repeated 20-30 times. The intercellular contacts in the skin, moreover, are sealed with the densely packed and well organized blend of lipids. The stratum corneum therefore not only protects the organism from infections but also precludes an efficient uptake of antigens through the skin. This fact, which is advantageous from the point of allergy, prevented successful immunization or vaccination through the intact skin to date.

The largest drugs on the market in any transdermal delivery device are smaller than 350 Da (Cevc, G. Drug delivery across the skin, Exp. Opin. Invest. Drugs (1997) 6: 1887-1937), as only such molecules can cross the tiny, self-sealing pores in the skin. The latter normally are less than 1 nm wide, when hydrophilic, or narrower, when hydrophobic. Organisms such as helminths therefore gain access into the body by penetrating the skin by using their biochemical machinery for the purpose of 'drilling holes' through the organ. Naturally occurring micro-lesions and shunts (such as pilosebaceous units) are available in the skin as well. However, they only cover up 0.1% to 0.5% of the skin surface and, consequently, do not contribute much to transcutaneous transport the fact notwithstanding that bacteria typically exploit such a route for a topical infection (Strange, P., Skov, L, Lisby, S., Nielsen, P. L., Baadsgard, O. Staphylococcal enterotoxin B applied on intact normal and intact atopic skin induces dermatoma. Arch. Dermatol. (1996) 132: 27-33.)

Only a few haptens exposed on the skin elicit a cutaneous immune response. This confirms that only sufficiently small molecules from a large load of the topically deposited haptens can find their way into the skin in an appreciable quantity. Such haptens then first irritate the organ and finally may cause hypersensitivity and contact dermatitis (Kondo, S., Sauder, D. N. Epidermal cytokines in allergic contact dermatitis. J. Am. Acad. Dermatol. (1995) 33: 786-800; Nasir, A., Gaspari, A. A. Contact dermatitis. Clinical perspectives and basic mechanisms. Clin. Rev. Allergy and Immunol. (1996) 14: 151-184). The problem is most serious with the low molecular weight chemicals or with the pharmaceuticals combined with skin irritants, such as skin permeation enhancers (Cevc, 1997, op. cit.). Large molecules seldom are allergenic on the skin, owing to their limited ability to cross the barrier. A Th2 response to a highly immunogenic ovalbumin (Wang, L.-F., Lin, J.-Y., Hsieh, K.-H., Lin, R.-H. Epicutaneous exposure of protein antigen induces a predominant Th2-like response with IgE production in mice. J. Immunol. (1996) 156: 4079-4082.) or to Cholera toxin (Glenn, G. M., Rao, M. Matyas, (1998) 391: 851; Glenn, G. M., Scharton-Karsten T, Vasell R, Mallet C. P., Hale T. L. and Alving C. R. Transcutaneous Immunization with Cholera toxin Protects Mice Against Lethal Mucosal Toxin Challenge. J. Immunol (1998) 161: 3211-3214.) was possible only after an epicutanous exposure to a large amount of such proteins and was fairly weak. Moreover, the stratum corneum elimination from the skin was a prerequisite for producing detectable quantities of the specific antibodies against adenoviruses encoding the human carcinoembryonic antigen or human GM-CSF gene in 96% or 43%, respectively, of epicutaneously treated C57BL/6 mice (Deng, H., Qun, L., Khavari, P. A. Sustainable cutaneous gene delivery. Nature Biotechnology (1997) 15: 1388-1390.).

No protection against the above mentioned or other epicutaneously employed antigens was reported to date. Antibodies against diphtheria or tetanus toxoid, and bovine serum albumin, which were generated by applying the antigens on the skin of BALB/c mice in combination with cholera toxin (Glenn at al., 1998, op. cit.) resulted in a very weak immune response without the adjuvant. Even after the inclusion of Cholera toxin (CT), the average specific antibody titre for diphtheria and tetanus antigens was around 50× and between 70× and 4000× (depending on the inclusion of individual data points), respectively, below that elicited by cholera toxin per se (Glenn at al., 1998, op. cit.). The corresponding absolute respective titre values were 14±17 and 8±16; the anti-BSA titre was approximately 11±11 (average value +/− standard deviation as calculated from the published figures). No therapeutic or prophylactic effect was demonstrated for these low titres, which shows that the path towards simple non-invasive vaccination is not at all straightforward. The more recent paper published by the same group (Glenn et al., 1998b) demonstrated protection against CT after transnasal challenge which does not allow any conclusion with regard to protection obtainable by transdermal vaccination.

Earlier publications report on the deliverance of proteins across the skin, several orders of magnitude more efficient than in the above mentioned study, as judged by the titres, exploiting mechanosensitive and hydrosensitive, self-regulating carriers (Transfersomes) (for a review, see Cevc, 1997, op. cit.). For potent antigens this induced antibody titres that were comparable with those elicited by subcutaneous protein injections: in the case of BSA, the absolute titre of IgG was around 200 in either case (Paul, A., Cevc, G. Non-invasive administration of protein antigens. Epicutaneous immunization with the bovine serum albumin. Vaccine Res. (1995) 4: 145-164) and for gap junction protein titres between 15.000 and 100.000 were measured (Paul, A., Cevc, G., Bachhawat, B. K. Transdermal immunization with large proteins by means of ultradeformable drug carriers. Eur. J. Immunol. (1995) 25: 3521-3524; Paul, A., Cevc, G., Bachhawat, B. K. Transdermal immunization with an integral membrane component, gap junction protein, by means of ultradeformable drug carriers, Transfersomes. Vaccine (1997) 16: 188-195.). Yet, the generation of a protective immune response was not demonstrated in either of these publications.

As is known today, the activity of Th1 or Th2 cells plays an important role in immune response: Th1 cells promote mainly the cell-mediated immunity, phagocyte-mediated host defense, but also the production of antigen specific IgG2a in mice. In contrast, Th2 cells tend preferentially to support phagocyte independent host-response, IgG1, IgE and IgA immunoglobulin generation.

The Th1 or Th2 basis of an immune response, that is, the differentiation into Th cell subtypes, not only depends on cytokines and the activity of other regulatory molecules (Luger, T. A., Schwarz, T. The role of cytokines and neuroendocrine hormones in cutaneous immunity and inflammation. Allergy (1995) 50: 292-302; Lohoff, M., Gessner, M., Bogdan, C., Roellinghoff, M. The Th1/Th2 paradigm and experimental murine Leishmaniasis. Int. Arch Allergy Immunol. (1998) 115: 191-202.); the nature of antigen presenting cells and antigen amount used also play an important role. Cytokines are produced transiently by almost all eukaryotic cells and act via specific cell-surface receptors. Indeed, every cell in the skin, after appropriate stimulation, can release such (glyco)protein factors or express their receptors. Most cytokines are pluripotent and can induce each other or else influence the expression of relevant receptors. This allows cytokines to act in synergistic, additive or antagonistic fashion, within the framework of so-called cytokine cascade (Luger & Schwarz, 1995; op. cit.).

The role of different cells in immunoactivation after cutaneous antigen application is as yet incompletely understood (Luger & Schwarz, 1995; op. cit.; Lohoff et al., 1998, op. cit.). Langerhans cells, located in the suprabasilar skin region, are believed to play the main role in immunopresentation. These cells first bind and process the antigens, then migrate from the epidermis into the lymphatic vessels, and further into the proximal, draining lymph node, bearing the digested antigens with them. During the process Langerhans cells undergo phenotypical and functional alterations and differentiate into (lymphoid) dendritic cells which finally offer the antigens to naive $CD4^+$ T cells that have entered the lymph nodes through the high endothelial venules. In contrast, the other two major types of antigen presenting cells in the skin, macrophages and B lymphocytes, first require activation in order to present antigens and stimulate T cells. Antibodies may be presented to T cells by the venular endothelial cells, and perhaps by certain basic cells of the skin as well.

It is clear, for example, that keratinocytes can augment the local inflammation by producing a plethora of proinflammatory cytokines, including IL-1α, GM-CSF and TNFα (Pastore, S., Fanales-Belaso, E., Abbanesi, C., Chinni, L. M., Giannetti, A., Girolomoni, G. Granulocyte macrophage colony stimulating factor is overproduced by keratinocytes in atopic dermatitis: Implications for sustained dendritic cell activation in the skin. J. Olin. Invest. (1997) 99: 3009-3017). Keratinocyte derived cytokines are also critical for the maturation of Langerhans cells into potent antigen presenting cells (Nasir & Gaspari, 1996, op. cit.). The extent to which the former cells directly participate in antigen presentation (Kondo & Sauder, 1995, op. cit.) is unknown but the production of inhibitory cytokines, such as IL-10, non-functional IL-12 and TGFβ, by keratinocytes is an established fact (Nasir & Gaspari, 1996, op. cit.).

The fibroblast pool in the skin also contains cellular subsets that are involved in antigen processing. For example, one subset of fibroblasts is recruited selectively by cytokines at the inflammation site in scleroderma (Fries, K. M., Blieden, T., Looney, R. J., Sempowski. G. D., Silvera, M. R., Willis, R. A., Phipps, R. P. Evidence of fibroblast heterogeneity and the role of fibroblast subpopulations in fibrosis. Clin. Immunol. Immunopathol. (1994) 72: 283-292.).

It has been reported previously that epicutaneous antigen application produces a different immune response than the more conventional routes of administration through the oral cavity or the nose. For example, after repeated epicutaneous ovalbumin exposure on the skin anti-ovalbumin IgE-s are prominent (Wang et al., 1996, op. cit.). Using bovine serum albumin as a model antigen on the skin, an unusually strong IgA production was previously observed (Paul et al., 1997, op. cit.), but no consistent picture of the interdependency between the details of epicutaneous antigen presentation and the resulting immune response emerged to date.

Numerous and different cells participate in mounting an immune response against the cutaneously delivered macromolecules. As has been stated above, the approaches taken so far have not led to the establishment of a convincing strategy for generating a protective immune response. This may be due to the fact that the prior art strategies, such as antigen injection, have not assisted in dissecting the immune response obtainable by applying antigens to the skin to an extent that allows for devising a directed and protective immune response. For example, it is known that antigen injection, as any lesion or other kind of skin perturbation, including the presence of chemical irritants, releases various cytokines from the skin (which not only is the heaviest organ in the body but also makes out the major part of the body immune system). This maximizes the strength, but prevents the fine tuning, of cutaneous immune response, which is also sensitive to the nature of antigens used. High impact vaccine delivery profits from this effect.

Material transport across the skin by means of ultradeformable carriers is just the opposite of said high-impact delivery approach, as it reportedly does not affect the skin. It is believed that this is due to the fact that such hydrosensitive, ultradeformable bodies—so called Transfersomes™ (Cevc, 1997, op. cit.), penetrate the stratum corneum through 'virtual channels' between corneocytes, adjusted to the shape of the cells (Schätzlein, A., Cevc, G. Non-uniform cellular packing of the stratum corneum and permeability barrier function of intact skin: a high-resolution confocal laser scanning microscopy study using highly deformable vesicles (Transfersomes). Br. J. Dermatol. (1998) 138: 583-592.). It was proposed that Transfersomes push the cells in the skin and intercellular lipids apart during the process, preferentially at the sites of weakest contact. The passages thus generated seem to be approximately 20-30 nm wide, on the average. They cover several percent (~4%) of the skin surface (Schätzlein & Cevc, 1998, op. cit.), the draining of adjacent surface not included. This is much more than the normal shunt area (~0.1%), which explains the quantitative differences between the anti-BSA titres measured after antigen administration with ultradeformable carriers (Paul & Cevc, 1995, op. cit.) or by using Cholera toxin as an adjuvant (Glenn et al., 1998a, b, op. cit.).

Virtual channels in the skin opened by the carriers appear to be sufficiently wide to let the carriers as well as material associated with them pass through the barrier without significantly perturbing the organ. However, repeated insulin delivery across the skin by means of ultradeformable carriers was found not to induce antibodies against the protein (Cevc, G., Gebauer, D., Schätzlein, A. Blume, G. Ultraflexible Vesicles, Transfersomes, Have an Extremely Low Permeation Resistance and Transport. Therapeutic Amounts of Insulin Across the Intact Mammalian Skin. Biochim. Biophys. Acta (1998) 1368: 201-215.)

The technical problem underlying the present invention was therefore to establish a means that allows for the successful induction of a medically useful transdermal immune response. The solution to said technical problem is achieved by providing the embodiments characterized in the claims.

Accordingly, the present invention relates to a transdermal vaccine comprising (a) a transdermal carrier which is a penetrant, suspended or dispersed in an aqueous solvent, in the form of a minute fluid droplet surrounded by a membrane-like coating of one or several layers of at least two different substances or two different forms of a substance with the tendency to aggregate, said substances or forms of a substance differing by at least the factor of 10 in solubility in a, preferably aqueous, liquid medium, such that the average diameter of homo-aggregates of the more soluble substance or form of the substance or the average diameter of the hetero-aggregates consisting of both said substances or forms of said substance is smaller than the average diameter of homo-aggregates of the less soluble substance, and/or wherein the more soluble component tends to solubilise the penetrating droplet and wherein the content of such component amounts to up to 99 mol-% of the concentration required to solubilise the droplet or else corresponds to up to 99 mol-% of the saturating concentration in the un-solubilised droplet, whichever is higher, and/or wherein the elastic deformation energy of the droplet surrounding the membrane-like coating is at least 5× lower, more preferably is at least 10× lower and ideally is more than 10× lower than that of the red blood cells or of the phospholipid bilayers with fluid aliphatic chains, (b) a compound which specifically releases or specifically induces molecules with cytokine or anti-cytokine activity or exerts such an activity, either of which resulting in the desired, medically useful immune response, and (c) an antigen, an allergen, a mixture of antigens, and/or a mixture of allergens.

As regards the above recited values of up to 99%, it is to be noted that values below 50% of the former relative concentration are often used. Even more advantageously values below 40 rel-% or even around and below 30 rel-% are chosen, whereas with the droplets that cannot be solubilised by the more soluble component relative concentrations that exceed the above mentioned ones by the factor of up to 2 are preferred.

In the context of this invention, the term "pathogen" refers to an entity which through its presence in or on the body leads to or promotes a pathological state which, in principle, is amenable to or could profit from a preventive, curative or adjuvant immunotherapy. This includes pathogens causing microbial diseases such as extracellular bacteria, including pus-forming cocci, such as *Staphylococcus* and *Streptococcus*, gram-negative bacteria, such as *Meningococcus* and *Gonococcus* species, species of *Neisseria*, gram negative bacteria, including enteric organisms such as *E. coli, Salmonella, Shigella, Pseudomonas, Diptheria, Bordetella Pertussis*, and gram-positive bacteria (e.g. *Bacillus pestis*, BCG), particularly anaerobes, such as the *Clostridium* species (e.g. *Clostridium tetani, Clostridium perfringens, Clostridium novyi, Clostridium septicum*); a number of bacteria and all viruses, which survive and replicate within host cells; this latter group encompasses mycobacteria (e.g. *M. tuberculosis*) and *Listeria monocytogenes*, retro- and adenoviruses, including but not limited to hepatitis virus, (human) immunodeficiency virus, herpes viruses, small-pox, (chicken-pox), influenza, measles, mumps and polio viruses, cytomegalovirus, rhinovirus, etc., and various fungi prospering inside host cells; parasites including animal parasites, such as protozoa and helminths, and ectoparasites, such as ticks and mites. The pathogens further include *Brucella* species (e.g. *B. melitensis, B. abortus, B. suis, B. canis, B. neotomae, B. ovis*), the causative agent for cholera (e.g. *Vibrio cholerae*), *Haemophilus* species like *H. actinomycetemcomitans, H. pleuropneumoniae*, as well as pathogens triggering paratyphoid, plague, rabies, tetanus and rubella diseases. Pathogens in this invention, furthermore, are assumed to include, but are not limited to, the eukaryotic cells or their parts that cause various neoplasiae, auto-immune diseases and other pathological states of the animal or human body which do not result from microbial infections. Parts of certain pathogens, especially various microbial toxins, have porin-like properties and, consequently, may have some capability to cross the mucosa or to increase the flexibility of penetrant membranes.

The term "specifically" in combination with "releases" or "induces" denotes the fact that the compound interacts with cells capable of releasing cytokines by a receptor-mediated triggering of this cytokine release or induction. This specific release or induction is in contrast to an unspecific release or induction that is, for example, obtained by an intradermal injection.

The term "allergen" is used in this invention to describe materials of endogenous or xenogenic, e.g., animal or plant, origin which result in an undesired immune response of the body exposed to such an allergen, often resulting in an acute hypersensitivity reaction. Allergising microbes or parts thereof (e.g. of mite), parts of plants (e.g. pollen) or animal (e.g. hair and skin debris), but also man made and inorganic substances belong to this group. On the other hand, nearly any part of the human body, if incorrectly processed by or exposed to the body's immune system, can result in an auto-immune response and lead to the allergic reaction to such a substance. In the narrower interpretation, used when so stated, an allergen is a substance, a group, or an arrangement of substances causing immediate hypersensitivity reactions in the body that could be diminished, or even eliminated, by an immunotherapy, whether done non-invasively through the skin or not.

The term "(therapeutic) vaccination" in the context of this invention describes any kind of therapeutic immunization, whether done after the disease has been already established, to improve a clinical situation, or else for the purpose of preventing a disease. Such a vaccination can involve single or repeated administration(s) of the vaccine of the invention.

Therapeutic vaccination will either prevent a pathological situation and/or improve a clinical situation. When applied as a preventive agent, it will generally result in a protective immune response.

Immunization denotes any kind of provoking an immune response, irrespective of whether said response is therapeutic or non-therapeutic.

An "antibody" or an "immunoglobulin" denotes an IgA, IgD, IgE, IgG, or IgM, including all subtypes, such as IgA1 and IgA2, IgG1, IgG2, IgG3, IgG4. Their "derivatives" include chemical, biochemical and otherwise obtainable derivatives, such as genetically engineered antibody derivatives. Fragments include, e.g., single chain fragments, Fc-, Fab-F(ab')$_2$- and other parts of Ig-s, independent of whether they are of endogenous, xenogenic, (semi)synthetic or recombinant origin. Also comprised by the invention are complexes of two or more of the above-recited antibodies, derivatives or fragments.

An "antigen" is a part of a pathogen or an allergen in its natural form or after fragmentation or derivatisation. More generally, the word antigen denotes a macromolecule or a fragment thereof, any haptenic moiety (for example, a simple carbohydrate, complex carbohydrate, polysaccharide, deoxyribonucleic acid), in short, any molecule recognized by a body's antibody repertoire and possibly capable of antibody induction when administered in the system.

The term "a mixture of antigens and/or a mixture of allergens" means, in accordance with the present invention the combination of at least two antigens or allergens. It is envisaged that also mixtures of antigens and allergens, comprising at least one antigen and at least one allergen, can be used according to the present invention.

The term "cytokine", as used in the present invention, denotes cytokines, such as IL-1, IL-2, IL-3, IL4, IL-5, IL-6, IL-7, IL-8, IL-9, IL-10, IL-11, IL-12, IL-13, IL-14, IL-15, IL-16, IL-17, IL-18, with all subtypes, such as IL-1α and IL-1β, tumor necrosis factor (TNF), transforming growth factor (TGF-β and -α), Type I and II interferons (IFN-α1, IFN-α2, (IFN-ω), IFN-β, IFN-γ), migration inhibitory factor, MIF, c-kit ligand, granulocyte macrophage colony stimulating factor (GM-CSF), monocyte macrophage colony stimulating factor (M-CSF), granulocyte colony stimulating factor (G-CSF), chemokines, etc., as well as all functional derivatives of any of these molecules.

Cytokines that mediate natural immunity particularly well include type I interferons (IFN-α and IFN-β), tumor necrosis factor (TNF), interleukin-1 (IL-1α and IL-1β), interleukin-6 (IL-6) and leukocytes attracting and activating chemokines. The process relies on antiproliferative (e.g. with IFN-s), proinflammatory (e.g. with TNF, IL-1) or co-stimulatory (e.g. with IL-6) action, amongst other. Cytokines which best mediate lymphocyte activation, growth and differentiation include interleukin 2 (IL-2), interleukin-4 (IL-4) and transforming growth factor (TGF). Such cytokines, consequently, not only can affect target growth but, moreover, influence the activation of, and thus the production of other cytokines by, the cells which finally may play a role in therapeutic action.

Cytokines that mediate immune-mediated inflammation, which heavily relies on the cell-mediated response, are interferon-gamma (IFN-γ), lymphotoxin (TNF-β, interleukin-10 (IL-10), interleukin-5 (IL-5), interleukin-12 (IL-12) and, probably, migration inhibition factor. Leukocyte growth and differentiation are most affected by interleukin-3 (IL-3), c-kit ligand, granulocyte-macrophage colony stimulating factor (GM-CSF), macrophage or granulocyte colony stimulating factor (M-CSF or G-CSF) and interleukin-7 (IL-7).

The term "immunoadjuvant" is used here to describe any substance which supports, augments, stimulates, activates, potentiates or modulates the desired immune response of either cellular or humoral type, specifically in the case of prophylactic treatment by increasing the antigen specific immune response of any kind and in the case of therapeutic treatment often by supporting cell-mediated immunity. This can be achieved by the addition of suitable cytokines, their blends or antagonists, or less directly by the chemical irritation of the skin, when this contributes directly or indirectly to the release of cytokines from the skin or other involved peripheral tissues, or else by catalyzing or promoting the biosynthesis of the molecules in the tissue which then lead to such action, provided that the final outcome is an increased success of vaccination, that is of prophylactic and/or therapeutic action of used antigen. The class of immunoadjuvants which indirectly contribute to the useful cytokine pool includes small chemical entities with an allergenic potential, such as certain allergenic (metal) ions, including but not limited to LiCl, $HgCl_2$. molibdenum, acids, bases and other irritating compounds, such as dicyclohexylmethane-4,4'-diisocyanate, ditrocarb (diethyldithiocarbamate), 2,4-dinitrochlorobenzene, isoprinosine, isophoronediisocyanate, levamisole, (phenyl)oxazolone and alike, Swansonine, sizofran, phthalic anhydride, thymopentin, (fatty) alcohols, (fatty) amines, (fatty) ethers, ricin, or other suitable amphiphiles, many surfactants and chemical skin permeation enhancers, as well as derivatives or combinations thereof; furthermore, (low molecular weight) fragments of or derivatives from microbes, including lipopolysaccharides (such as LPS), cordfactor (trehalose-dimycolate) and other polysaccharides attached to membranes, when used in sufficient quantity, acetylmuramyl-alanyl-isoglutamin, and larger fragments of microbes, including bacterial exo- and endotoxins, or enterotoxins, such as cholera toxin and the heat labile toxin (HLT) of *E. coli*, and their macromolecular fragments, such as A-chain derivatives most, if not all, of which seem to posses ADP-ribosylating activity, the high potency immunoadjuvant LT holotoxin, etc., cell-wall skeleton, attenuated bacteria, such as BCG, etc. Less established examples include clostridial toxin, purified protein derivative of *M. tuberculosis*, LT-R192G, Fibronectin-binding protein I of *Streptococcus pyrogenes*, outer membrane protein of group B *Neisseria meningitidis* (GBOMP), various other peptidoglycanes, etc. Immunoadjuvants, in other words, include molecules that alter the uptake or presentation of antigens, activate or increase the proliferation of antigen specific lymphocytes, or interfere with the dominant control mechanism in the immune response, not just in the skin but also in the other immunocompetent tissues. (The mucosal adjuvant activity of ADP-ribosylating bacterial enterotoxins is a well established and known example for this.) On the other hand, molecules which change the (relative) concentrations of cytokines or other immunoadjuvants, such as anti-immunoadjuvant antibodies or other agonists or antagonists of immunoadjuvants, also are immunoadjuvants in the sense of this invention. The same is true for molecules which affect lymphocyte homing, such as various selectins (LECAMS, e.g., various CD62-s), GlyCAM-1, MadCAM-1, VCAM-1, ICAM-1, hyaluronate, etc., and other chemokines, such as RANTES or MCP-1. Endogenous group of immunoadjuvant furthermore comprises histamines, transfer factor, tuftsin, etc. As many of the above mentioned immunoadjuvants do not have sufficient potency to ensure the desired effect after the non-invasive immunization at too low, and sometimes too high, concentration or on their own, the functional definition of an adjuvant used in this work includes a fortiori sufficient and such modulation of cytokine concentration and distribution pattern in the body that results in mounting the desired therapeutic or prophylactic immune response. If required to gain clarity said modulation and its extent must be determined in a dedicated experiment, in which the specific cytokine levels are determined, for example.

"Immunoadjuvant manipulation" denotes a non-chemical treatment of the skin, such as skin rubbing, pressing, heating, exposing to an electrical or mechanical, e.g., ultrasound, field, etc., or even an injection of a non-immunogenic formulation in the skin, provided that such treatment releases immunoadjuvant compounds from the skin or other peripheral immuno-active tissues or else reduces the concentration/duration of action of antagonists to the desired vaccination. However, the term "immunoadjuvant manipulation" also denotes, in accordance with the present invention, a pretreatment of the skin with immunomodulators and/or cytokines and/or cytokine releasing factors, like, inter alia, histamine.

The term "immunogen" denotes a hapten coupled to an immunological carrier or an antigen, free or associated with a carrier, which is capable of inducing an immune response.

"Immuno-tolerance" denotes the lack or, more generally, the reduction of an undesired immune response to an antigen.

Th1 (T-helper cell type I) related antibodies include IgG2a, IgG2b and IgG3.

Th2 (T-helper cell type II) related antibodies comprise the classes of IgG1, IgG4 and IgE.

The term "two forms of a substance" in connection with this invention means two ionization states or salt forms of the same substance, two different complexes of such substance, etc.

"Non-invasive administration" or "non-invasive delivery" denotes application on or transport through an intact barrier, in the biological applications dealt with in this disclosure, through intact skin.

"Penetration" describes a non-diffusive motion of relatively large entities across a barrier. This process typically relies on the penetrant adaptation to the otherwise confining pores in the barrier and also may involve a penetration induced decrease in the barrier resistance, such as pore widening or channel opening; the process does not depend, however, primarily on the penetrant concentration gradient across the barrier.

"Permeation" refers to a diffusive motion across the semipermeable barriers. The prime example for this is the transport of molecules or molecular aggregates under the influence of a permeating species concentration gradient across the barrier.

A penetrant, consequently, is an entity comprising a single molecule or an arrangement of molecules too big to permeate through a barrier but capable to cross the barrier owing to the penetrants adaptability to the shape and/or diameter of the otherwise confining passages (pores) of a barrier. This adaptability is seen from the fact, for example, that penetrants more than twice bigger than the pore diameter will cross the bilayer without being fragmented down to the pore size. A permeant, on the other hand. is an entity that can permeate through the semi-permeable barrier, such as the skin. A penetrant in an external field experiences a driving force proportional to the nominal penetrant size and to the applied field, which may occur naturally. Such a force, which on the intact, non-occluded skin is believed to originate from the water concentration gradient across the stratum corneum, can result in a penetrant motion through the barrier, including the skin, if the force is strong enough either to deform the penetrant or else to widen the passages in the barrier sufficiently to elude the problem of size exclusion, or both.

For further definitions, especially such pertaining to the penetrants in terms of complex body deformability, the corresponding mechanism of action, lists of interesting penetrant ingredients or selected agents it is referred to the issued or pending patents (DE 41 07 152, PCT/EP91/01596 (published as WO/1992/003122 and equivalent to U.S. Pat. No. 6,165,500 A), PCT/EP96/04526 (published as WO/1998/17255 and equivalent to U.S. Publication No. 2002/048596), DE 44 47 287). Detailed information relevant for the manufacturing process and penetrant loading with the antigenic (macro) molecules and/or immunoadjuvants, which are too big to permeate through the barrier, can be found in international patent application PCT/EP98/06750 (published as WO 00/24377 and equivalent to U.S. Publication No. 2008/279815).

Typically, the less soluble amongst the aggregating substances forming a carrier is a lipid or lipid-like material, especially a polar lipid, whereas the substance which is more soluble in the suspending liquid and which increases the droplet adaptability belongs to surfactants or else has surfactant-like properties. The former ingredient, typically, is a lipid or lipid-like material from a biological source or a corresponding synthetic lipid or any of its modifications, such lipid often belonging to the class of pure phospholipids with the chemical formula 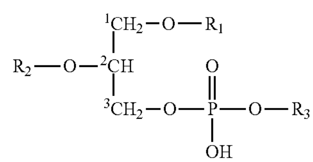 where $R_1$ and $R_2$ is an aliphatic chain, typically a $C_{10-20}$-acyl, or -alkyl or partly unsaturated fatty acid residue, in particular, an oleoyl-, palmitocloyl-, elaidoyl-, linolenyl-, linolenoyl-, arechidoyl-, vaccinyl-, lauroyl-, myristoyl-, palmitoyl-, and stearoyl chain, and where $R_3$ is hydrogen, 2-trimethylamino-1-ethyl, 2-amino-1-ethyl, $C_{1-4}$-alkyl, $C_{1-5}$-alkyl substituted with carboxy, $C_{2-5}$-alkyl substituted with hydroxy, $C_{2-5}$-alkyl substituted with carboxy and hydroxy, or $C_{2-5}$-alkyl substituted with carboxy and amino, inositol, sphingosine, or salts of said substances, said lipid comprising also glycerides, isoprenoid lipids, steroids, sterines or sterols, of sulphur- or carbohydrate-containing lipids, or any other bilayer forming lipids, in particular half-protonated fluid fatty acids, and preferably is selected from the group of phosphatidylcholines, phosphatidylethanolamines, phosphatidylglycerols, phosphatidylinositols, phosphatidic acids, phosphatidylserines, sphingomyelins or other sphingophospholipids, glycosphingolipids (including cerebrosides, ceramidepolyhexosides, sulphatides, sphingoplasmalogens), gangliosides or other glycolipids or synthetic lipids, in particular with or else with corresponding sphingosine derivatives, or any other glycolipids, whereby two similar or different chains can be esterified to the backbone (as in diacyl and dialkenoyl compound) or be attached to the backbone with ether bonds, as in dialkyl-lipids.

The surfactant used, normally, is nonionic, zwitterionic, anionic or cationic, especially a fatty-acid or -alcohol, an alkyl-tri/di/methyl-ammonium salt, an alkylsulphate salt, a monovalent salt of cholate, deoxycholate, glycocholate, glycodeoxycholate, taurodeoxycholate, taurocholate, etc., an acyl- or alkanoyl-dimethyl-aminoxide, esp. a dodecyl-dimethyl-aminoxide, an alkyl- or alkanoyl-N-methylglucamide, N-alkyl-N,N-dimethylglycine, 3-(acyldimethylammonio)-alkanesulphonate, N-acyl-sulphobetaine, a polyethyleneglycol-octylphenyl ether, esp. a nonaethylene-glycol-octylphenyl ether, a polyethylene-acyl ether, esp. a nonaethylen-dodecyl ether, a polyethylene-glycol-isoacyl ether, esp. a octaethylene-glycol-isotridecyl ether, polyethylene-acyl ether, esp. octaethylenedodecyl ether, polyethyleneglycol-sorbitane-acyl ester, such as polyethylenglykol-20-monolaurate (Tween 20) or polyethylenglykol-20-sorbitanmonooleate (Tween 80), a polyhydroxyethylene-acyl ether, esp. polyhydroxyethylene-lauryl, -myristoyl, -cetylstearyl, or -oleoyl ether, as in polyhydroxyethylene-4 or 6 or 8 or 10 or 12, etc., -lauryl ether (as in Brij series), or in the corresponding ester, e.g., of polyhydroxyethylen-8-stearate (Myrj 45), myristate-, -laurate, linoleate-, linolenate-, palmitoleate- or -oleate type, or in polyethoxylated castor oil 40, a sorbitane-monoalkylate (e.g. in Arlacel or Span), esp. sorbitane-monolaurate, -myristate, -linoleate, -linolenate-, -palmitoleate- or -oleate, an acyl- or alkanoyl-N-methylglucamide, esp. in or decanoyl- or dodecanoyl-N-methylglucamide, an alkyl-sulphate (salt), e.g., in lauryl-, myristoyl, palmitoyl, oleoyl-, palmitoleoyl-, linolenyl-, linoleoyl-, vaccinyl-, or elaidoyl-sulphate, sodium deoxycholate, sodium glycodeoxycholate, sodium oleate, sodium taurate, a fatty acid salt, with similar preference for aliphatic chains as given above, a lysophospholipid, such as n-octadecylene(=oleoyl)-glycerophosphatidic acid, -phosphorylglycerol, or -phosphorylserine, n-acyl-, e.g., lauryl, myristoyl, palmitoyl, oleoyl-, palmitoleoyl-, elaidyl-, vaccinyl-, linoleyl-, linolenyl-glycero-phosphatidic acid, -phosphorylglycerol, or -phosphorylserine, or a corresponding short, double chain phospholipid, such dodecyl-phosphatidylcholine, or else is a surface-active polypeptide. It is important to realize, however, that complexes of polar lipids with other amphipats often can take the role of surfactants in the coating of a carrier and that different ionization or salt states of polar lipids differ widely in their properties. It therefore stands to reason that two different physicochemical states of the same (polar) lipid mixed together in a membrane will produce a highly deformable carrier satisfying the conditions of this work.

More general information on lipid suspensions can be found in handbook dealing with 'Liposomes' (Gregoriadis, G., Hrsg., CRC Press, Boca Raton, Fla., Vols 1-3, 1987), in the book 'Liposomes as drug carriers' (Gregoriadis, G., Hrsg., John Wiley & Sons, New York, 1988), or in the laboratory manual 'Liposomes. A Practical Approach' (New, R., Oxford-Press, 1989). The properties of phospholipids which can be used conveniently to prepare bio-compatible immunopenetrants are reviewed in 'Phospholipids Handbook' (Cevc, G., ed., Dekker, New York, 1995).

It may be convenient to adjust the pH value of a formulation immediately after preparation or just before its application. Such an adjustment should prevent the deterioration of individual system components and/or drug carriers under the conditions of initial pH without sacrificing physiological compatibility. To neutralize a penetrant suspensions it is reasonable to use biocompatible acids or bases to prepare buffers with a pH value between 3 and 12, frequently between 5 and 9 and most often between 6 and 8. Physiologically acceptable acids are, for example, diluted aqueous solutions of mineral acids, such as hydrochloric acid, sulphuric acid, or phosphoric acid, or organic acids, such as carboxyalkane acids, e.g. acetic acid. Physiologically acceptable bases are, for example, diluted sodium hydroxide, suitably ionized phosphoric acid, etc.

If required, immunogen suspension can be diluted or concentrated (e.g. by ultracentrifugation or ultra-filtration) before the application; additives can also be given into the suspension at this time or before. The additives are often selected amongst substances that reduce the formulation sensitivity to ambient stress, including microbicides, anti-oxidants, antagonists of undesired enzyme action, in case cryo-preservants, thickening agents, etc. However, after any system manipulation, the carrier characteristics should be checked and, if required, readjusted.

In accordance with the present invention it was surprisingly found that macromolecular antigens associated with ultradeformable lipid aggregates described herein (immuno-penetrants) can cross artificial porous barriers as well as the skin, despite the fact that the average diameter of said penetrants exceeds the average pore/channel diameter, and that such immuno-penetrants can elicit a therapeutic or prophylactic immune response, provided that said immuno-penetrants are associated with compounds that display cytokine activity or induce the generation in and/or the release of cytokines from the skin, and/or other immunocompetent organs in the body. Alternatively, said compounds antagonize cytokine activity. This latter embodiment advantageously directs the immune response into a Th1 or Th2 dependent immune response by blocking the respective other route. The antigen carriers described in this invention maintain sufficient stability before and during the process. It was further surprisingly found that the resulting immune response is not directly proportional to the applied dose, which implies that the amount of antigen may be varied. Said amount should be well chosen for optimum effect. Choosing optimum amount or range of antigen is well within the skills of the person knowledgeable in the art taking into account the teachings of this specification.

The at least bi-component immuno-aggregates used as carriers in the vaccines of this invention excel in high deformability and most often have the form of vesicles a with highly flexible membrane. Although such carriers have been employed in immunization protocols before, it was unexpected that the previously postulated carrier immunoadjuvancy does not eliminate the need to include compounds with cytokine activity or the appropriate antagonists thereto, preferably IL-4, IL-10, TGF-β. IL-5, IL-6, IL-9 and IL-13; or, after the pre-stimulation of T-cell receptor, also IL-1 in order, to achieve the desired protective immune response. By the same argument, IL-12, IFN-γ and lymphotoxin (LT or TNF-β) are advantageously included to promote the Th1 response and thus to favor the cell-mediated immune response and to provide a means for treating viral and other parasite diseases or for promoting the immuno-tolerance. For example, a combination of IFNγ, IL-12 and anti IL-4 or simply the addition of IL-12 is expected to revert Th2 response toward Th1 type. More broadly speaking, increasing the relative amount of IL-12 and IL-4 in the beginning of an immune response in favor of the former is proposed to be useful to promote Th1 response also in the case of penetrant mediated immunization, and vice versa, whereas IL-2 is going to support NK and B cells growth, to stimulate antibody synthesis, and to affect the magnitude of T-cell dependent immune response in general. Thus, whereas the prior art demonstrated that antibody titres could be induced by using suitable carriers in combination with antigen and optionally with immunoadjuvants, the immuno responses obtained were not demonstrated to be protective.

A particular advantage of the present invention is due to the fact that it was surprisingly found that the transfer of the penetrant described in this invention does not lead to an essential disturbance of the cytokine composition within the skin. In other words, the transfer of these carriers through the skin will per se not induce any essential release of cytokines. It is therefore possible to study now and to trigger a desired immuno response by including into the vaccine of the invention a compound that specifically induces or releases cytokines from cells in the skin or other organs that are competent to release such cytokines. Fine tuning of a desired immuno response thus may be possible. Alternatively, a compound having or exerting cytokine activity can be included into the vaccine of the invention. Further, an antagonist of cytokine activity may be used that specifically prevents the action of such cytokines. In this embodiment, the immuno response may advantageously be directed towards the Th1 or Th2 pathway. It is important to note that these compounds specifically induce or release cytokines in dependence on antigen properties. They are thus distinguished from adjuvants which, in accordance with the present invention, unspecifically and broadly support an immuno response.

Application of the vaccine of the present invention allows, in conclusion, therefore the fine tuning of a desired immuno response to a given antigen, the nature of which also plays a given role, of course. This immuno response may be enhanced by an unspecific immuno response, triggered, for example, by an adjuvant. The option of fine tuning the immuno response is in particular advantageous over the prior art using only the injection of vaccines because the injection process per se will heavily and unspecifically disturb the relative cytokine concentrations in the skin.

Consideration of the above mentioned criteria not only provides the basis for a suitable kind of immunopresentation to the cells of the skin and peripheral immune system (by the carriers) but also ensures such immunoprocessing that will either predominantly generate antigen-neutralizing antibodies in the body, will give rise to the cell-mediated immune response, or else will result in the gradual development of tolerance against the antigens or in the specific promotion of cell-mediated immunity.

In accordance with the present invention, it was also found that the outcome of noninvasive transcutaneous vaccination is strongly affected by the immuno-penetrant (antigen carrier) composition. Using antigens of different purity, unexpectedly, resulted in vastly different immune response. This was reflected in the observation that organisms with a similar overall titre revealed diverse levels of protection, probably due to the different final antigen isotype patterns.

Furthermore, the addition of a conventional, low molecular weight immunoadjuvant, monophosphoryl lipid A, not only made the result of epicutaneous immunization more robust, as documented by the smaller standard deviation in the measured antibody titres published before. Using this immunoadjuvant in immuno-carriers also, unexpectedly and contrary to previous experience obtained in mice, increased the secretion of IgG2b, and less strongly of IgG2a, but did not enhance IgA production. As the presence of IgG1, which is a Th1-like immunoglobulin, is inferred to be essential for, at least murine, protection against the tetanus toxin, the role of lipid A or bacterial antigens was thus revealed for the first time. For the future medical and commercial use of teachings disclosed in this invention it is important to realize that a high (specific) antibody titre does not necessarily imply a good protection result; to achieve the desired and sufficient protection the right kind and relative amount of certain antibody isotypes is required, such that will give prevalently Th1- or Th2-type of immune response (see previous discussion), as the case should be.

Basic formulations suitable for achieving the desired goals are known in the art: see, e.g., DE 41 07 152, PCT/EP91/01596 (published as WO/1992/003122 and equivalent to U.S. Pat. No. 6,165,500 A), PCT/EP96/04526 (published as WO/1998/17255 and equivalent to U.S. Publication No. 2002/048596), DE 44 47 287, for more detailed or complementary information. The vaccine of this invention is not useful just for prophylactic or therapeutic vaccination but, moreover, is applicable for the treatment of allergy and for obtaining immunity against microbes, including extracellular and intercellular bacteria, viruses and parasites in the human and veterinary medicine.

In combination with the above mentioned penetrants, an antigen, such as an immunoactive substance, is transported across the barrier in form of a physical or a chemical complex with the former.

In order to profit from the pool of cytokines residing in the skin, a particularly useful method of vaccination is proposed in which an immunogen is applied on the skin after pretreating the organ by an immunoadjuvant manipulation as defined before.

It is particularly advantageous to use the readings from the above mentioned local immune response to a patch assessment for optimizing the details and the course of further allergen administration, and thus to positively affect the outcome of therapeutic or prophylactic vaccination. It is believed that such an approach could be used advantageously to reach or improve immuno-tolerance of the tested subject to an applied allergen.

If primary immunization is done invasively, typically by using a subcutaneous injection or some other suitable skin barrier perforating/destructing method, one expects to obtain high IgM levels but the subsequent, booster immunizations may then be done non-invasively as described in this invention.

Finally, several optimization methods are proposed which can be used to improve immunogens and vaccination based on highly deformable penetrants. Preferred is a method wherein the flux of penetrants associated with an immunogen through the various pores in a well-defined barrier is determined as a function of suitable driving force or pressure acting across the barrier and the data are then conveniently described by a characteristic curve which, in turn, is employed to optimize the formulation or application further. Its core is the determination of the flux of immuno-penetrants through the pores in a well-defined barrier as a function of suitable driving force or pressure, which acts across the barrier, and the resulting data analysis in terms of a characteristic curve which, in turn, can be employed to optimize the formulation or application further, based on comparison of different data sets. This includes comparison with the results pertaining to the immunogen-free penetrant suspensions of known skin penetration capability, reported for example by Cevc et al., (1998, op. cit.). In a complementary, preferred, embodiment various combinations of immunomodulants or of immunomodulating procedures are tested with regard to chiefly Th1- or Th2-related cytokine production and the results are then used to make a suitable choice for the final therapeutic or prophylactic application.

Vaccination is typically done at ambient temperature, but lower or higher temperatures may also be suitable. They make particular sense with the formulations comprising synthetic substances which are rigid between the room and the skin or other barrier temperature.

Manufacturing temperature is normally chosen in the 0 to 95° C. range. Preferably, one works in the temperature range 10-70° C., most frequently at temperatures between 15° C.

and 45° C., under all circumstances below the temperature at which any important formulation ingredient would undergo an irreversible change in composition or physical state. The skin temperature is normally 32° C. Other temperature ranges are possible, however, most notably for the systems containing freezable or non-volatile components, cryo- or heat-stabilized formulations, etc.

If required to maintain the integrity and the desired properties of individual system components, carrier formulations can be stored in cold (e.g. at 4° C.), with or without an associated antigen. Manufacturing and storage under an inert atmosphere, e.g. under nitrogen, is possible and sometimes sensible. The shelf-life of immunogen formulation can also be extended by using substances with only a small number of double bonds, that is, by a low degree of unsaturation, by the addition of antioxidants, chelators, and other stabilizing agents, or by preparing the immuno-penetrants ad hoc or in situ from a freeze dried or a dry mixture.

In a preferred embodiment of the vaccine according to the invention the compound which specifically releases or specifically induces molecules with cytokine or anti-cytokine activity and the antigen are associated with the penetrant.

In a further preferred embodiment of the vaccine according to the present invention the less soluble self-aggregating molecule is a polar lipid and the more soluble component is a surfactant or a surfactant-like molecule or else such form of polar lipid which is sufficiently soluble for the purpose of this invention.

In an additional preferred embodiment of the vaccine according to the present invention the average diameter of the penetrant is between 30 nm and 500 nm, preferably between 40 nm and 250 nm, even more preferably between 50 nm and 200 nm and particularly preferably between 60 nm and 150 nm.

The invention in one further preferred embodiment relates to a vaccine wherein total weight of droplets in the formulation for the use on human or animal skin is 0.01 weight-% (w-%) to 40 w-% of total mass, in particular between 0.1 w-% and 30 w-%, and most preferably between 5 w-% and 20 w-%.

In another preferred embodiment of the vaccine according to the present invention total antigen concentration is between 0.001 w-% and 40 w-% of the total penetrant mass, in particular between 0.01 w-% and 30 w-%, even better between 0.1 w-% and 20 w-% and most preferably between 0.5 w-% and 10 w-%.

In another preferred embodiment of the vaccine according to the present invention the formulation further comprises (da) a low molecular weight chemical irritant, and/or (db) a low molecular weight compound from a pathogen or a fragment or a derivative thereof.

In yet another preferred embodiment of the vaccine according to the present invention the compound exerting cytokine activity is IL-4, IL-3, IL-2, TGF, IL-6, IL-7, TNF, IL-1α and/or IL-1β, a type I interferon, preferably IFN-α or IFN-β, IL-12, IFN-γ, TNF-β, IL-5 or IL-10.

In one more preferred embodiment of the vaccine according to the present invention the compound displaying anti-cytokine activity is an anti-cytokine antibody or the corresponding active fragment, a derivative or an analogue thereof.

The term "active fragment or derivative thereof" in this connection means that the above-recited activity is essentially maintained or mimicked by the substance used.

In another preferred embodiment of the vaccine according to the present invention the antigen is derived from a pathogen.

In another particularly preferred embodiment of the vaccine according to the present invention said pathogen is selected from extracellular bacteria, including pus-forming cocci, such as *Staphylococcus* and *Streptococcus*, gram-negative bacteria, such as *Meningococcus* and *Gonococcus* species, species of *Neisseria*, gram negative bacteria, including enteric organisms such as *E. coli, Salmonella, Shigella, Pseudomonas, Diptheria, Bordetella Pertussis*, and gram-positive bacteria (e.g. *Bacillus pestis*, BCG), particularly anaerobes, such as the *Clostridium* species (e.g. *Clostridium tetani, Clostridium perfringens, Clostridium novyi, Clostridium septicum*), bacteria and viruses, which survive and replicate within host cells, comprising mycobacteria (e.g. *M. tuberculosis*) and *Listeria monocytogenes*, retro- and adenoviruses, including hepatitis virus, (human) immunodeficiency virus, herpes viruses, small-pox (chicken-pox), influenza, measles, mumps and polio viruses, cytomegalovirus, rhinovirus, etc., and fungi prospering inside host cells, parasites including animal parasites, such as protozoa and helminths, and ectoparasites, such as ticks and mites, or *Brucella* species (e.g. *B. melitensis, B. abortus, B. suis, B. canis, B. neotomae, B. ovis*), the causative agent for cholera (e.g. *Vibrio cholerae*), *Haemophilus* species like *H. actinomycetemcomitans, H. pleuropneumoniae*, as well as pathogens triggering paratyphoid, plague, rabies, tetanus and rubella diseases and pathogens that cause various neoplasiae, autoimmune diseases or are related to other pathological states of the animal or human body which do not necessarily result from pathogen infections.

In a preferred embodiment of the vaccine according to the present invention the allergen is of xenogenic or endogenic origin, derived from a microorganism, an animal or a plant which leads to an acute hypersensitivity reaction of the body exposed to the allergen, many such allergens stemming from mite, pollen, animal hair or skin debris, or belonging to the group of man made and/or irritating inorganic substances, or to such parts or components of the human body which were incorrectly processed by or exposed to the body immune system.

In a further preferred embodiment of the vaccine according to the present invention the concentration of each compound displaying cytokine activity used is selected to be up to 1000 times higher than the concentration optimum established in the corresponding tests with the antigen and immunoadjuvant chosen, performed by subcutaneously injecting the formulation or performing the tests in vitro, and preferably is up to 100×, more often up to 50× and even better up to 20× higher.

In a different preferred embodiment of the vaccine according to the present invention the pathogen extract or compound is a lipopolysaccharide, cord-factor (trehalose-dimycolate), muramyl dipeptide, or another (poly)saccharide or (poly) peptide identical to or resembling an immunologically active part of a membrane of a pathogen; an extract of a pathogen, including bacterial exo- and endotoxins, preferably cholera toxin or the heat labile toxin (HLT) of *E. coli*, an A-chain derivative, a component with an ADP-ribosylating activity, a peptidoglycane, a clostridial toxin, or a purified protein derivative of *M. tuberculosis*, LT-R192G, Fibronectin-binding protein I of *Streptococcus pyrogenes*, or outer membrane protein of group B *Neisseria meningitidis* (GBOMP); or bacterial or viral nucleic acids such as oligonucleotides containing unmethylated CpG dinucleotides.

In a particularly preferred embodiment of the present invention said lipopolysaccharide is lipid A or a derivative and modification thereof, such as monophosphoryl lipid A, or its analogue, such as a fatty derivative of saccharose.

In another particularly preferred embodiment of the vaccine according to the present invention the concentration of the pathogen compound derived from a pathogen is between 10× lower and up to 1000× higher than that otherwise used with the corresponding injected formulations employing similar antigen, the epicutaneously administered immunoadjuvant concentration more often differing from the injected immunoadjuvant concentration by the factor between 0.5 and 100, or better, by the factor between 1 and 50, and best between 2 and 25.

In still another particularly preferred embodiment of the vaccine according to the present invention the low molecular weight irritant is selected from the classes of allergenic metal ions, acids, bases, irritating fluids, (fatty-) alcohols, (fatty-) amines, (fatty-) ethers, (fatty-) sulphonates, -phosphates, etc., or other suitable solvents or amphiphiles, or from the group of surfactant-like molecules, often with the skin permeation enhancing capability, as well as derivatives or combinations thereof.

In a preferred embodiment of the vaccine according to present invention the concentration of a low molecular weight irritant is chosen to be by at least the factor of 2, more often by the factor of 5, and even better by the factor of 10 or more, below the concentration which in independent tests on the same or comparable subject is deemed to be unacceptable owing to the local irritation, as assessed by the methods and standards commonly used to test such an irritant.

In a further particularly preferred embodiment of the vaccine according to the present invention the allergen belongs to the class of inhalation allergens, including various pollen, spores, bits of animal hair, skin, feather, natural and synthetic textiles, wheat, (house) dust, including mite; food and drug allergens; contact allergens; injection, invasion and depot allergens, such as various (gastrointestine-resident) worms, echinococci, trichines, etc., parts of implantation material, etc.

In a preferred embodiment of the vaccine according to the present invention the applied dose of an antigen differs by the factor of 0.1 to 100 from the dose which otherwise would have to be injected in the process of immunization, but more often is in the range between 0.5 to 50, even better between 1 and 20 and ideally is less than 10× higher than that used with an injection.

In another preferred embodiment of the vaccine according to the present invention the applied penetrant dose is between 0.1 mg cm$^{-2}$ and 15 mg cm$^{-2}$, even more often is in the range 0.5 mg cm$^{-2}$ and 10 mg cm$^{-2}$, and preferably is between 1 mg cm$^{-2}$ and 5 mg cm$^{-2}$. It may also be advantageous to use different administration areas to control the applied immunogen dose, using easily accessible or sheltered body areas (such as the chest or back regions, arms, lateral side of the neck, e.g. behind the ears, or even in the scalp region) for the purpose.

In a different preferred embodiment of the vaccine according to the present invention said antigen is a pure or purified antigen. The use of highly purified antigens in the vaccine of the invention has turned out to be particularly advantageous for the generation of a protective immuno response.

The present invention further relates to a kit comprising, in a bottled or otherwise packaged form, at least one dose of the vaccine.

In a preferred embodiment according to the present invention the kit comprises at least one injectable dose of the antigen described above.

The present invention further relates to a method for generating a protective immune response on a mammal comprising vaccinating said mammal with a vaccine as described above.

In another preferred embodiment of the method according to the present invention different treatment areas are selected to control the applied immunogen dose and the outcome of therapeutic vaccination.

In one more preferred embodiment of the method according to the present invention a suspension of antigen-free penetrants is loaded with the antigen to be associated therewith during the day prior to an administration, preferably 360 min, more preferably 60 min and even more preferably 30 min before the administration of resulting formulation on the skin.

In a different preferred embodiment of the method according to the present invention the vaccine of the present invention is applied on the skin after pre-treating the organ by an immunoadjuvant manipulation, said manipulation comprising, for example, skin rubbing, pressing, heating, exposing to an electrical or mechanical, e.g. ultrasound field, etc., or injecting a non-immunogenic formulation in the skin, provided that any such treatment releases immunoadjuvant compounds from the skin or other peripheral immuno-active tissues or else reduces the concentration/duration of action of antagonists to the desired vaccination.

In a preferred embodiment of the method according to the present invention immunogen is applied in a non-occlusive patch. This embodiment can also be used for the purpose of assessing the skin reaction to an epicutaneously administered immunogen in the penetrant suspension, to which the former, at least originally, is allergic and which thus gives rise to an acute local hypersensitivity reaction, as seen, for example from the resulting flare, irritation, etc.

In another preferred embodiment of the method according to the present invention at least one dose of vaccine is administered.

This embodiment of the method of the invention includes the repeated administration of the vaccine of the invention. Repeated administration includes repeated administration on the skin or one or more administrations on the skin in combination with, e.g., parenteral administrations. In this connection, the kit of the invention may be advantageously used that comprises one or more containers or ampoules comprising the vaccine of the invention.

In a particularly preferred embodiment of the method according to the present invention said vaccine is administered as a booster vaccination.

In a most preferred embodiment of the method according to the present invention the primary immunization is done invasively, typically using a subcutaneous injection or some other suitable skin barrier perforating/destructing method, and the at least one subsequent, booster immunization is done non-invasively.

In a preferred embodiment of the method according to the present invention the vaccine is applied between 2 and 10, preferably between 2 and 7, even more preferably up to 5 and most preferably up to 3 times, when a non-allergenic antigen is used, or such a number of times, in the case of allergens, as is required either to achieve the desired immuno-tolerance, determined according to a suitable assessment method, or else to deem the effort as having failed.

In a particularly preferred embodiment of the method according to the present invention the time interval between the subsequent vaccinations is chosen to be between 2 weeks and 5 years, often between 1 month and up to 3 years, more frequently between 2 months and 1.5 years. In a further preferred embodiment, repeated immunogen administration is advocated to maximize the final effect of a therapeutic vaccination. It is proposed to use between 2 and 10, often between 2 and 7, more typically up to 5 and most preferred up to 3 immunizations, when a non-allergenic antigen is used, or such a number of times, in the case of allergens, as is required either to achieve the desired immuno-tolerance, determined as described above or another suitable assessment method, or else to deem the effort as having failed. The time interval between subsequent vaccinations should preferably be between 2 weeks and 5 years, often between 1 month and up to 3 years, more frequently between 2 months and 1.5 years, when a subject is being immunized for the first time. Rodents, such as mice and rabbits are advantageously immunized in 2 weeks interval, primates, e.g., monkeys and often humans, need a booster vaccination in 3-6 months interval.

In a preferred embodiment of the method according to the present invention the flux of penetrants that carry an immunogen through the various pores in a well-defined barrier is determined as a function of a suitable driving force or a pressure acting across the barrier and the data are then conveniently described by a characteristic curve which, in turn, is employed to optimize the formulation or application further.

The invention finally relates to the use of the transdermal carrier, the compound which specifically releases or specifically induces cytokine or anti-cytokine activity or exerts such an activity, the antigen or allergen, and optionally an extract or a compound from a microorganism or a fragment or a derivative thereof, and/or a low molecular weight chemical irritant as defined hereinbefore for the preparation of a vaccine for inducing a protective or tolerogenic immune response.

The figures show:

FIG. 1: Mixed micelles versus Transfersomes. The figure gives the data on survival of animals immunised epicutaneously with mixed micelles or Transfersomes loaded with purified TT, to illustrate aggregate size (stability) effect, since the over-destabilised Transfersomes normally disintegrate into the mixed lipid micelles.

Figure 2:
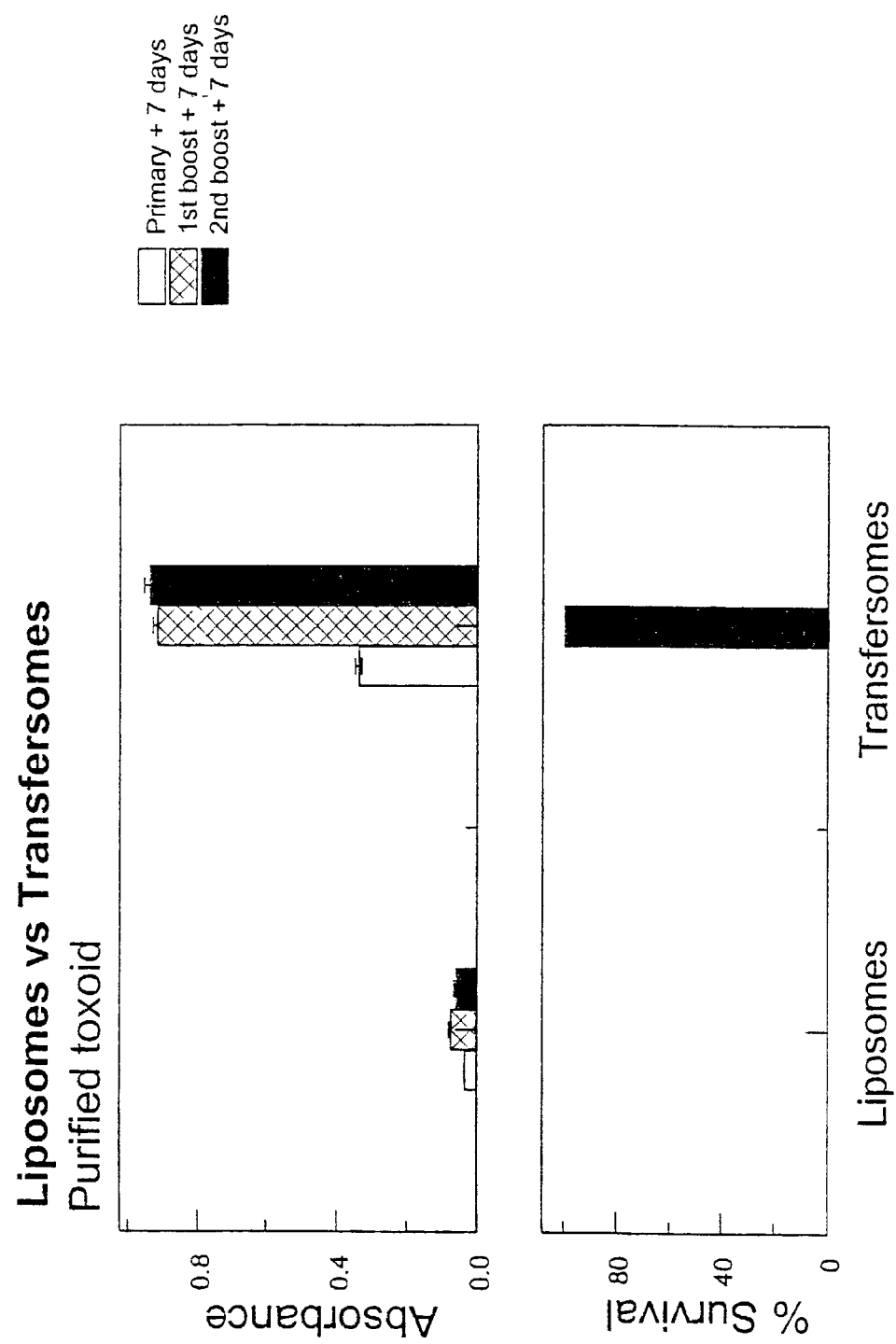

FIG. 2: Liposomes versus Transfersomes. A comparison is made between the immune response to conventional lipid vesicles (liposomes) and ultradeformable lipid vesicles (Transfersomes) carrying purified TT and applied on the skin. The information on corresponding specific antibody concentrations in serum (expressed as absorbance) is given in the upper panel.

Figure 3:
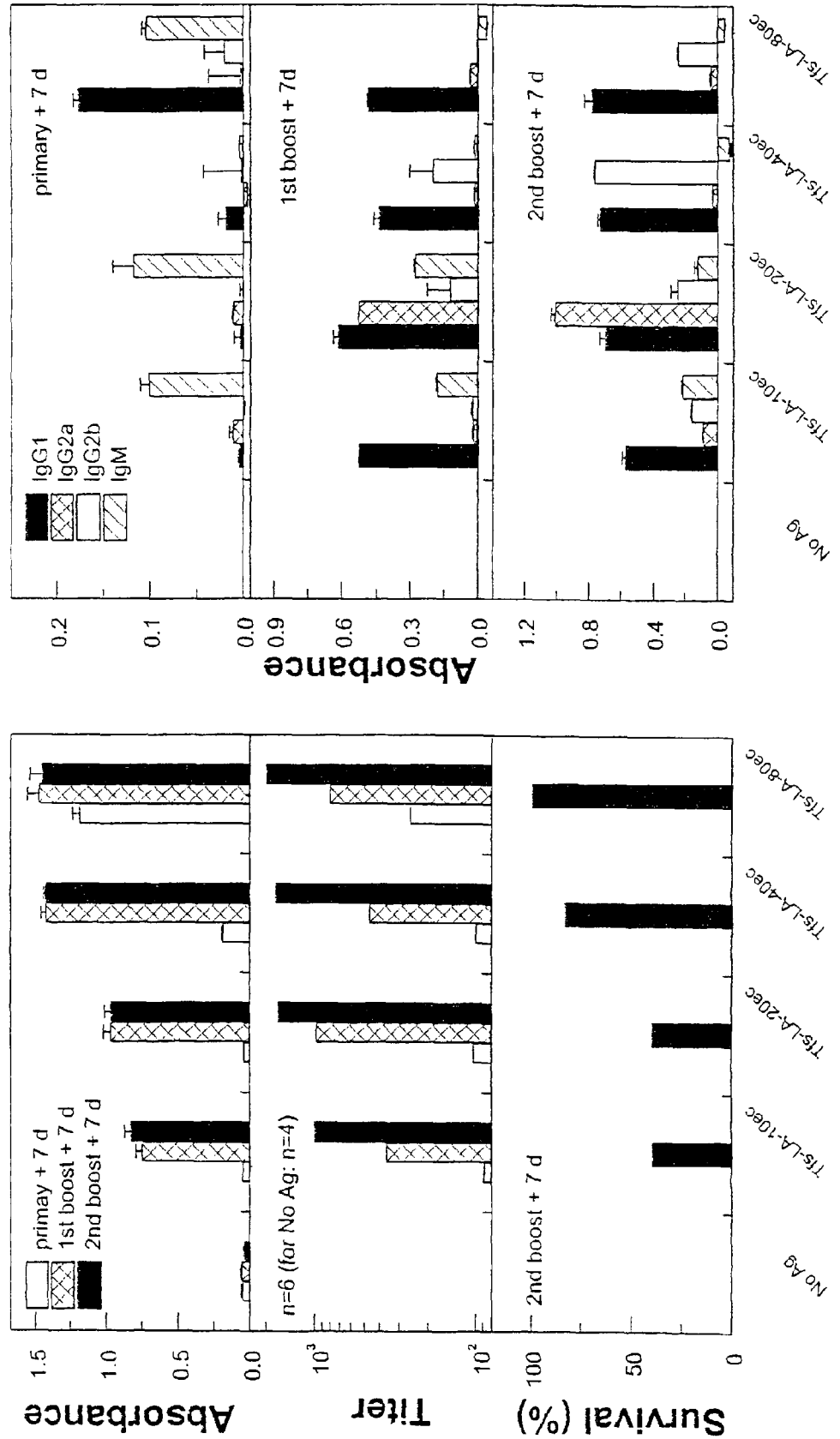

FIG. 3: Antigen dose effect. The figure illustrates the effect of increasing antigen dose on the outcome of epicutaneous immunisation by means of Transfersomes from SPC:NaChol (3.75:1) loaded with antigen and monophosphoryl lipid A (LA). The results are expressed as absorbance change, antibody titre, or animal survival, together with the corresponding specific antibody isotyping data. Antigen doses were 10, 20, 40 and 80 µg. 6 animals per each group except for No Ag (4 animals) were used.

Figure 4:
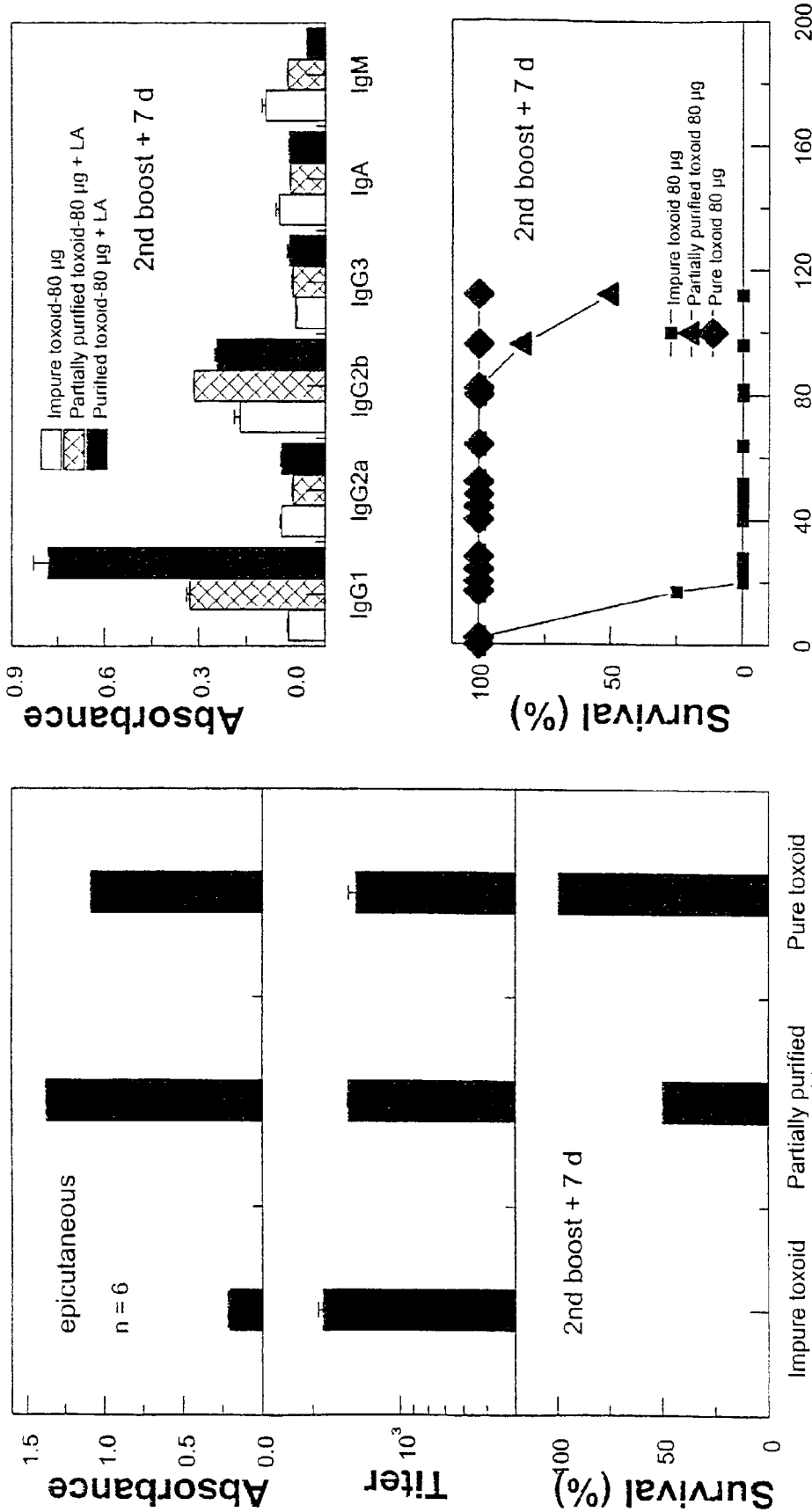

FIG. 4: Antigen purity effect. The figure highlights the effect of antigen purity on the result of epicutaneous immunisation with 80 µg tetanus toxoid and monophosphoryl lipid A (LA) in Transfersomes from SPC:NaCh (3.75:1), including information on time dependence of animal survival. All data were obtained after the 2nd boost+7 days.

Figure 5:
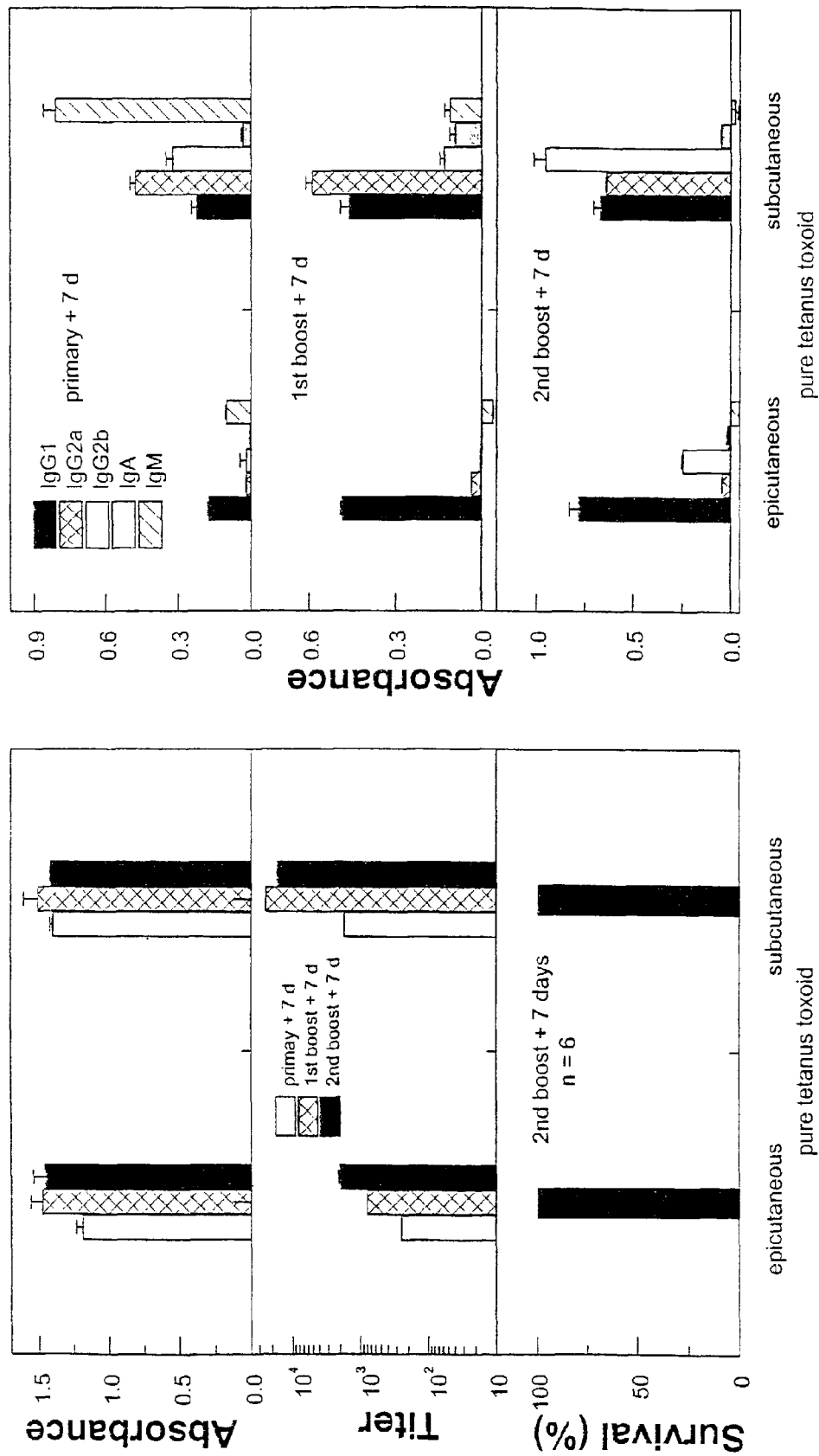

FIG. 5: Epicutaneous versus subcutaneous immunization. The figure compares the outcome of repeated invasive (subcutaneous) and non-invasive (epicutaneous) immunisation by means of TT in Transfersomes, including animal survival, serum concentration (in terms of absorbance), specific antibody titre, and antibody distribution pattern values.

Figure 6:
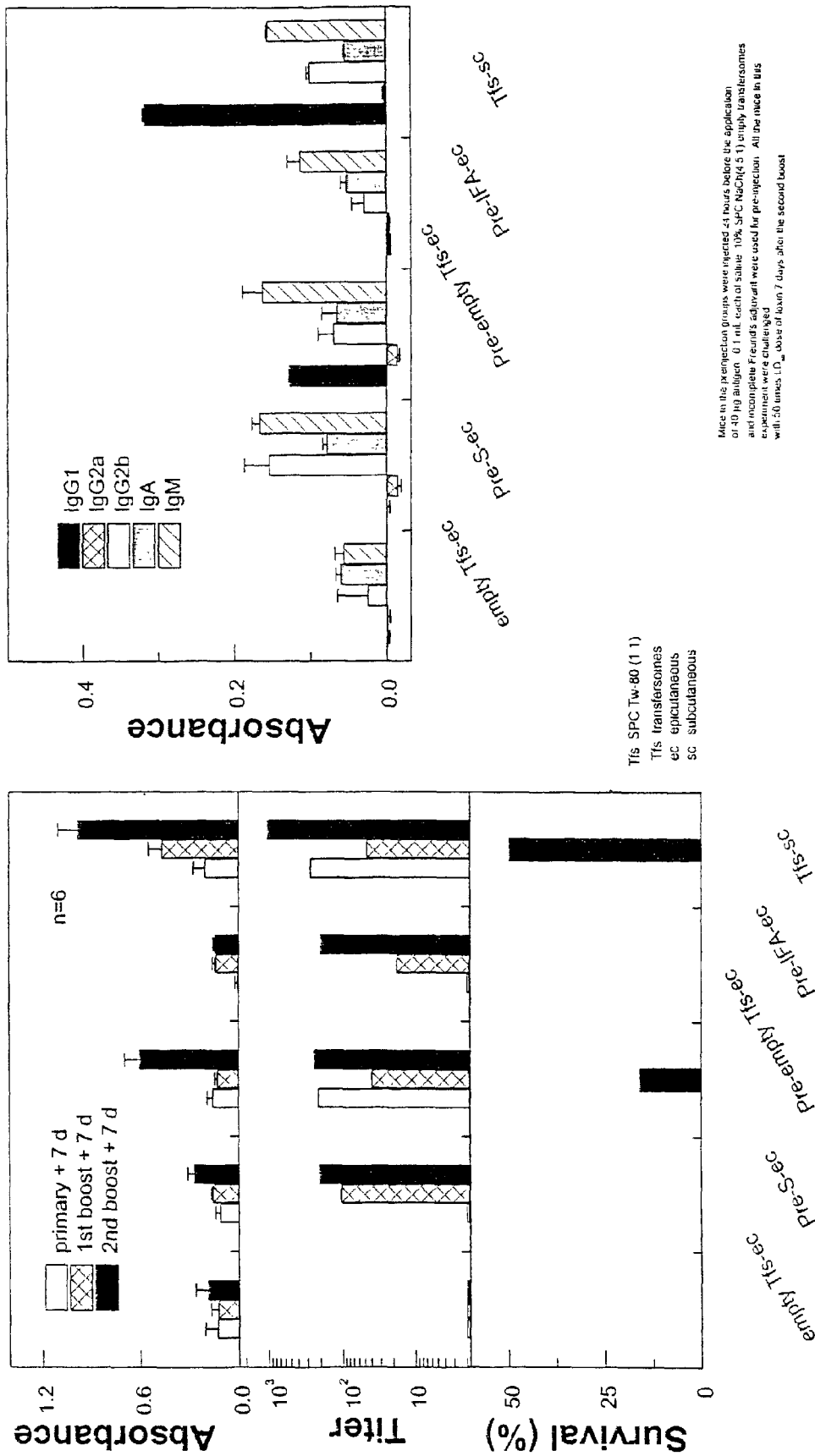

FIG. 6: Pre-injection effect. The figure illustrates the effect of skin pre-treatment (non-specific challenge) on the immune response following Transfersome (SPC:Tw-80 1:1) mediated TT (40 µg) delivery across the skin. Mice in the preinjection groups were injected 24 hours before the application of 40 µg antigen. 0.1 ml each of saline (pre-S), 10% SPC:NaCh 4.5:1 empty Transfersomes (Pre-empty Tfs), and incomplete Freund's adjuvant were used for pre-injection. All mice in this experiment were challenged with 50 times LD50 dose of toxin 7 days after the second boost. It means (ec) epicutaneous, (sc) subcutaneous, and (Tfs) Transfersomes.

Figure 7:
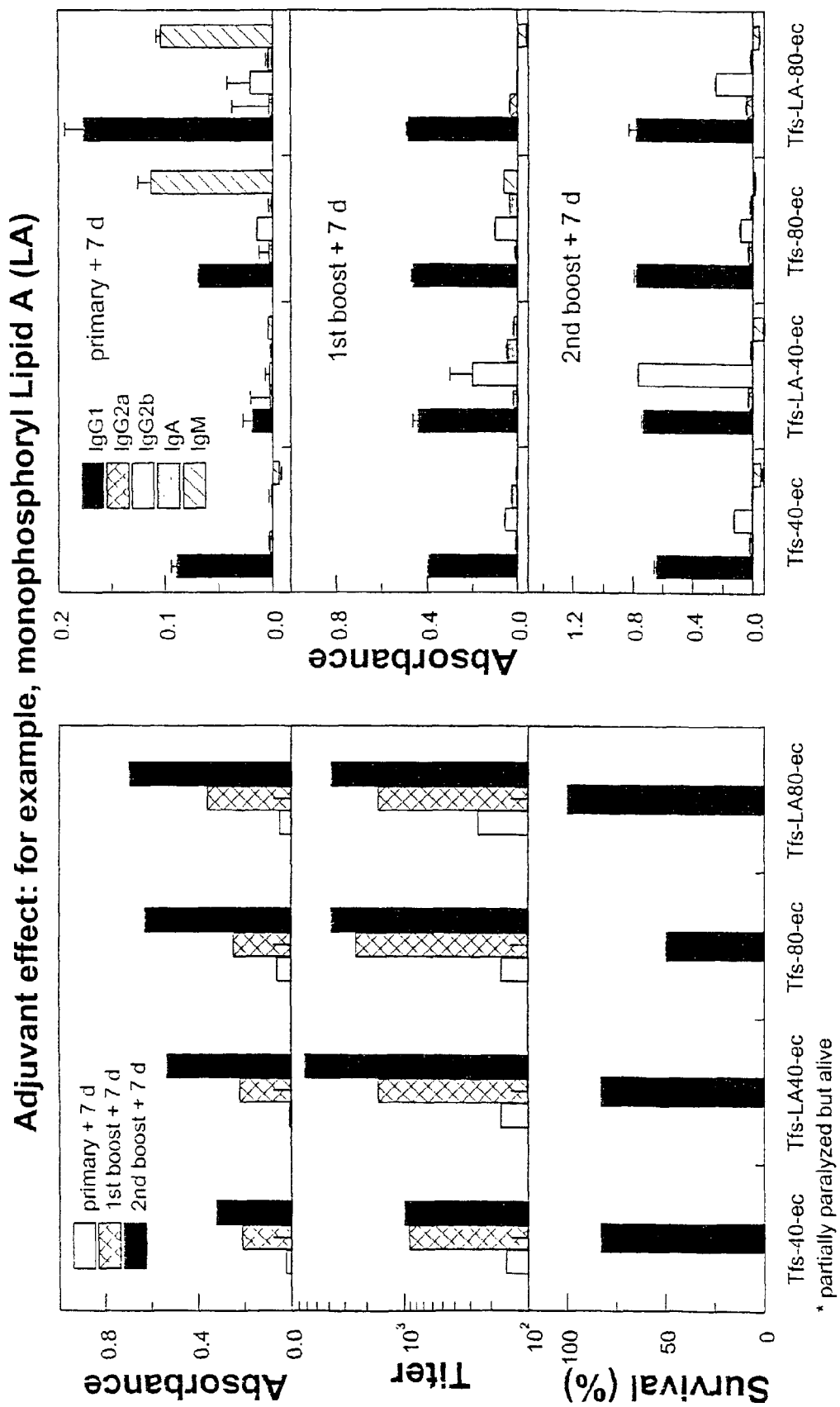

FIG. 7: Adjuvant effect: for example monophosphoryl lipid A. The figure focuses on adjuvant effect of a relatively low-molecular weight immuno-stimulator, monophosphoryl Lipid A (LA), delivered across intact skin together with TT in Transfersomes.

Figure 8:
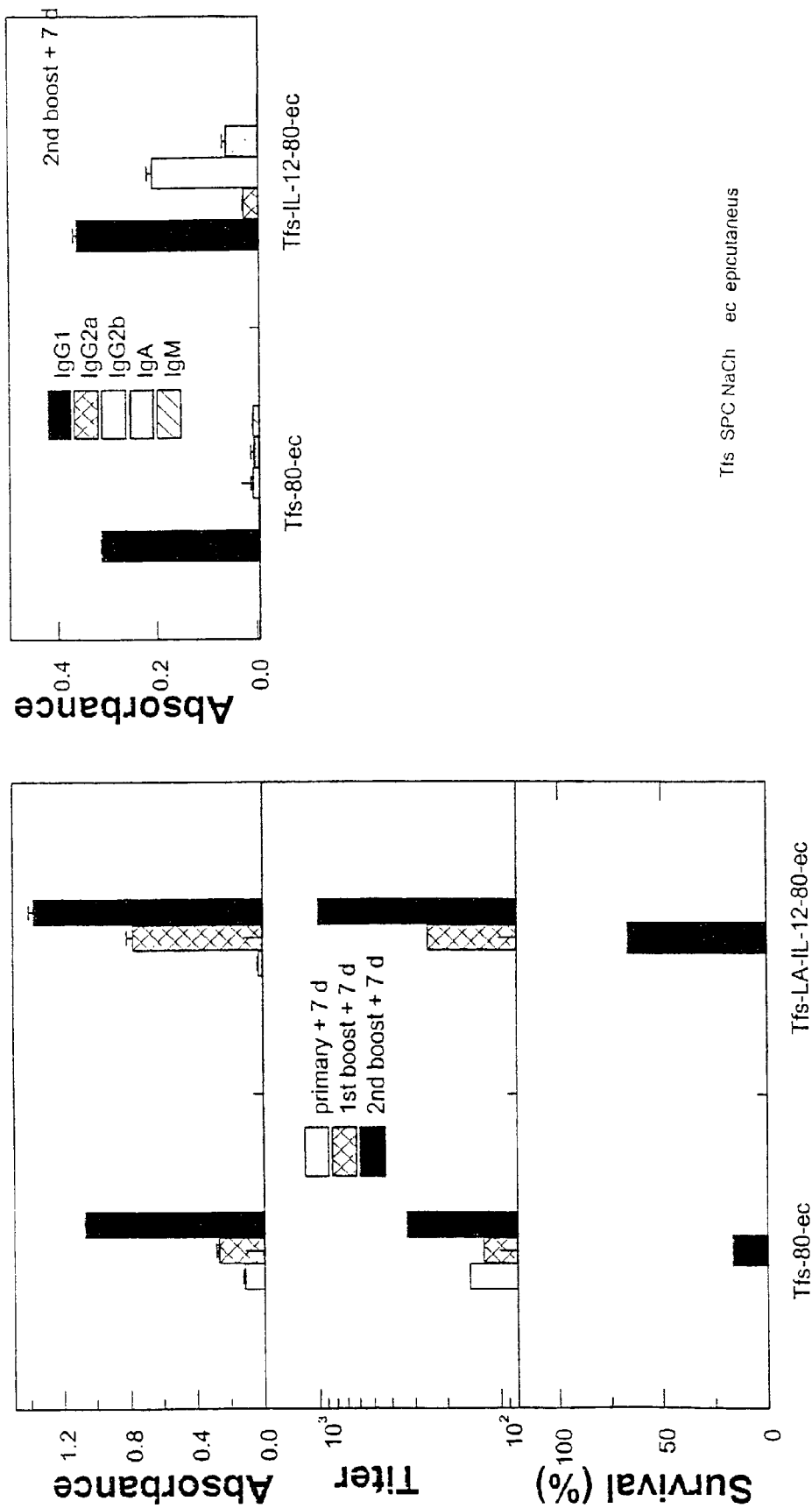

FIG. 8: Adjuvant effect: for example cytokine IL-12. The figure demonstrates the immuno-adjuvancy of a cytokine, interleukin-12 (IL-12) transported across the skin (ec) together with TT by means of Transfersomes from SPC: NaCh.

FIG. 9: Immunomodulant effect, for example cytokines. The figure deals with the immuno-modulation by various cytokines of the murine response against impure tetanus toxoid (TT) antigen delivered in Transfersomes non-invasively through the skin. Serum was collected for the assay on the $7^{th}$ day after $2^{nd}$ boost. No protection was observed in any of the groups.

Figure 10:
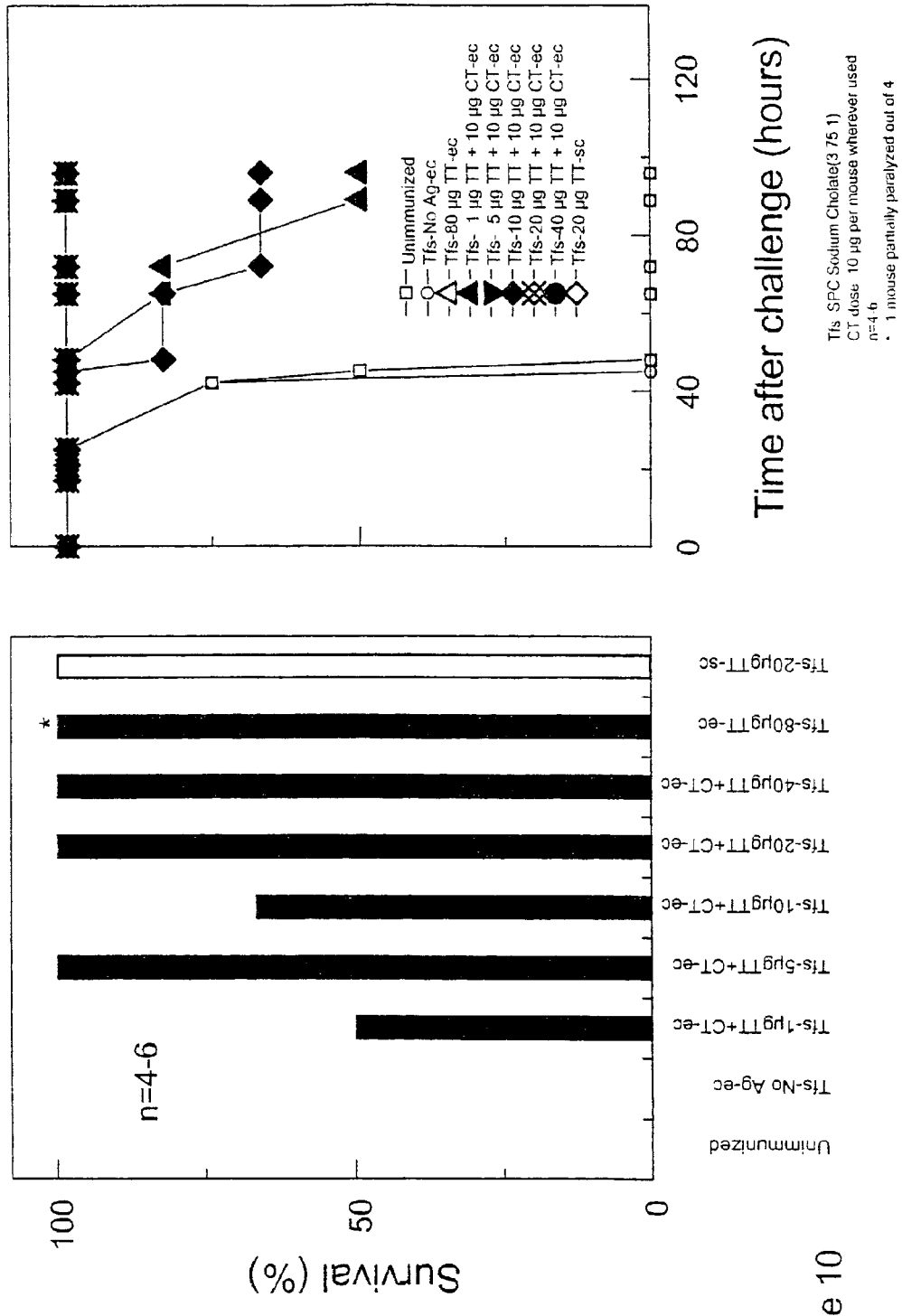

FIG. 10: Immunoadjuvant effect: for example cholera toxin (CT). The figure presents experimental evidence for the immune response stimulation of mice treated on the skin by pure tetanus toxoid (TT) in Transfersomes (SPC:NaCh 3.75: 1), when the carriers also include 10 µg cholera toxin (CT) to support the specific antibody production, and thus animal protection against an otherwise lethal challenge by the tetanus toxin. 4-6 animals per group were used. The asterisc indicates 1 paralyzed mouse out of 4.

FIG. 11 Adjuvant effect: for example heat labile toxin (HLT) from E. coli. The figure illustrates the use of heat labile toxin from E. coli as an immuno-adjuvant.

Figure 12:
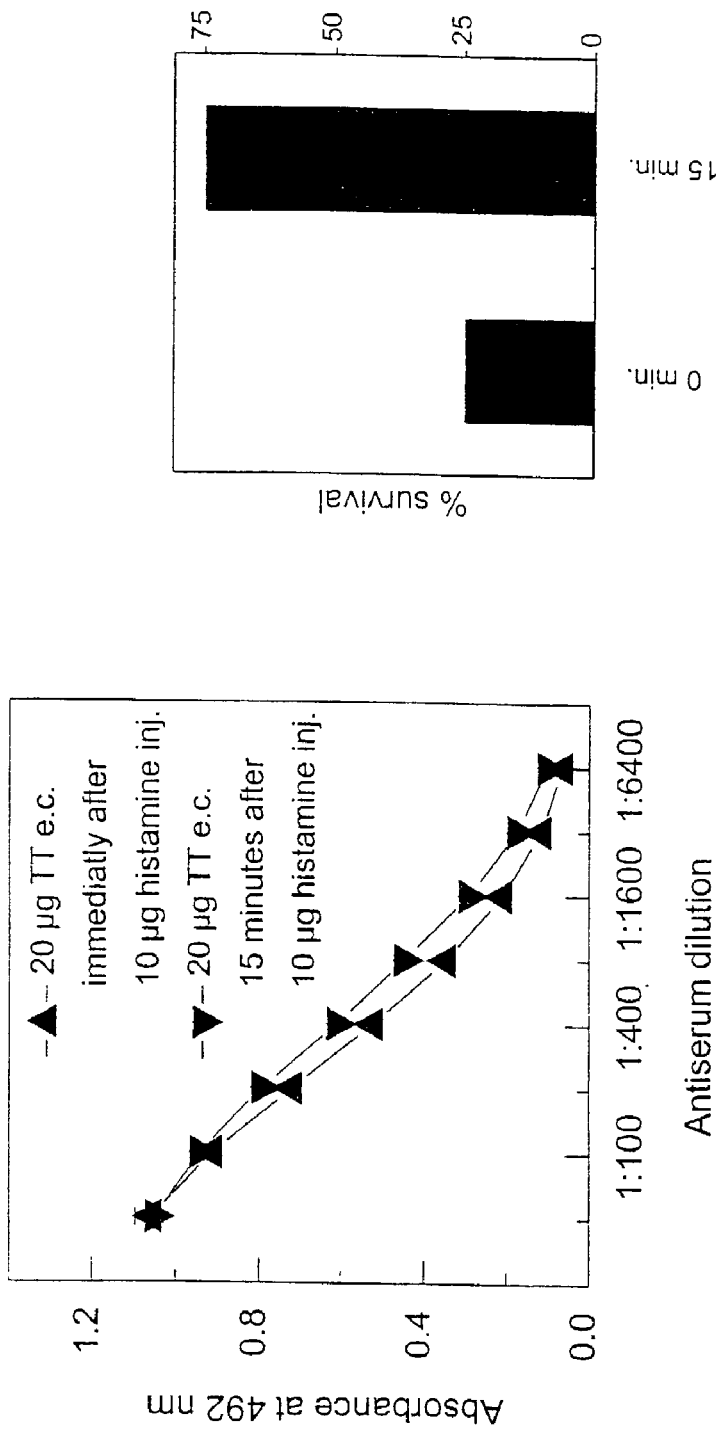

FIG. 12: Histamine effect: on anti-tetanus titer and survival after immunization with Transfersomes on the skin. The figure illustrates the immuno-modulating effect of local skin pre-treatment with histamine in combination with transdermal antigen application with Transfersomes.

Figure 13:
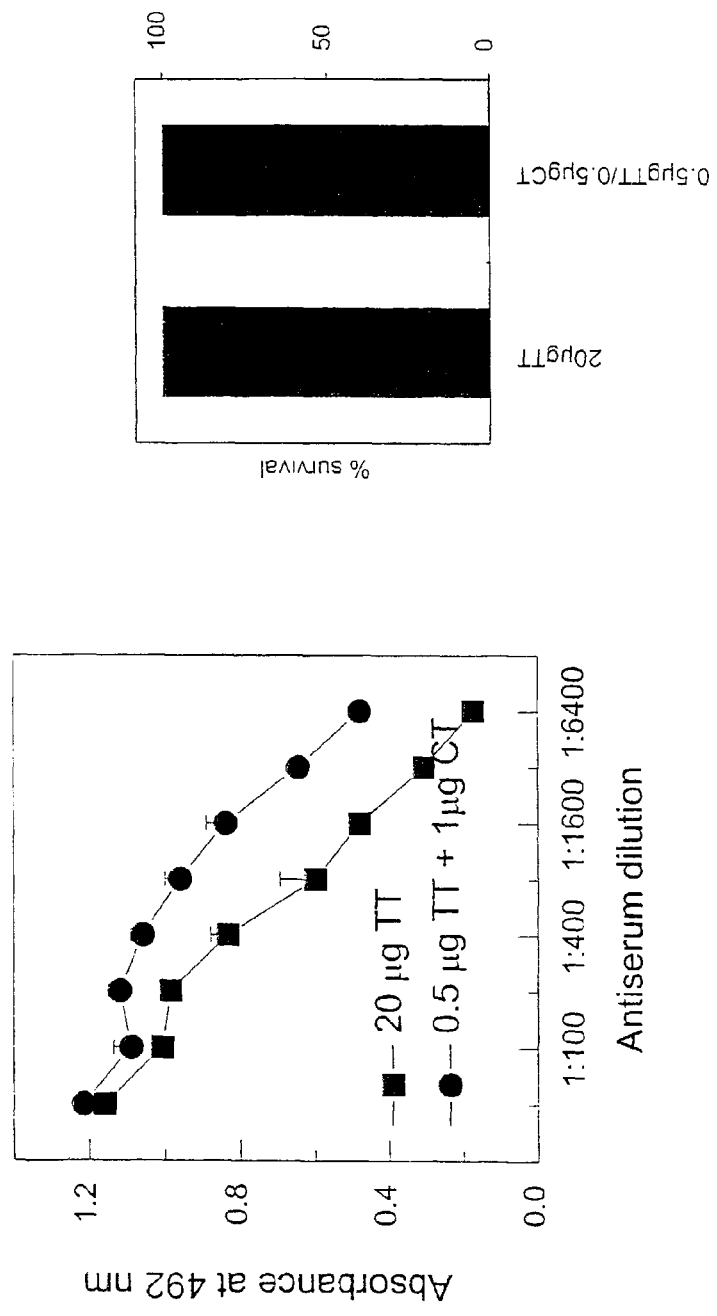

FIG. 13: Subcutaneous priming: effect on anti-tetanus titer and survival after epicutaneous boosts. The figure demonstrates the effect of subcutaneous priming on anti-tetanus titer and on the survival of epicutaneously vaccinated hosts.

FIG. 14: Bi-valent vaccines: Anti-Tetanus and anti-Cholera response to the administration of both antigens together in Transfersomes on the skin. The figure shows the effect of bi-valent vaccination with Tetanus Toxoid and Cholera Toxin used as antigens.

The examples illustrate but do not define the limits of the invention.

General Experimental Set-Up and Sample Preparation

Mice of Swiss albino strain (18-20 g) were obtained from The National Institute of Nutrition (Hyderabad, India). They were 8 to 12 weeks old at the time of first immunization and were normally kept in suspension cages in groups of 4 to 6. The animals had free access to standard chow and water. One day prior to an immunization, the application area on murine back was shaved carefully. The antigen was administered with a high precision pipette on the skin surface and left to dry out partially. To prevent immunogen abrasion, the animals were transferred into individual cages in which they were kept for 18 hours following each epicutaneous material administration.

General anesthesia was used to keep the test animals stress free and quiet during manipulations, including immunization. An injection of a mixture of Ketavet and Rompun (0.3 mL per mouse of an isotonic NaCl solution containing 0.0071% Rompun (Bayer, Leverkusen, Germany) and 14.3 mg/mL Ketavet (Parke-Davis, Rochester, N.Y.) into the peritoneal cavity was used for the purpose. This typically kept the animals asleep for app. 2 hours.

Immunogens

Ultradeformable immuno-carriers, or immuno-penetrants (immuno-Transfersomes), studied in this work, typically had the form of (oligo)bilayer vesicles. They contained biocompatible (phospho)lipids, such as phosphatidylcholine, and (bio)surfactants, such as sodium cholate or polysorbate (Tween 80), different compositions maintaining the high aggregate deformability being possible. Additional ingredients were monophosphoryl lipid A, with a versatile immuno-adjuvant activity, and antigens, as required and specified.

Conventional vesicles, liposomes, comprised soy phosphatidylcholine (SPC; Nattermann Phospholipids, Rhone-Poulenc Rorer, Cologne, Germany) and were prepared as described as follows. An organic lipid solution with or without the adjuvant monophosphoryl lipid A (MLA) at 0.04 mol-% relative to SPC was first dried under vacuum (10 Pa, overnight). The resulting lipid film was hydrated with a solution of tetanus toxoid (2.0 mg/mL; Accurate antibodies, NY, USA) in phosphate buffer (pH=6.5) to get a 10 wt-% lipid suspension. Crude suspension of lipid vesicles was extruded through the series of polycarbonate membranes with 800 nm, 400 nm, and 200 nm pores, to narrow down the final vesicle size distribution.

Highly deformable vesicles, Transfersomes, were prepared as described earlier (Paul et al., 1995 op. cit.). In short, an ethanolic SPC solution was mixed with sodium cholate (Merck, Darmstadt, Germany) (3.75/1 mol/mol) and the adjuvant, if required. The mixture was dispersed in 10 mM phosphate buffer (pH=6.5). This was done with tetanus toxoid present in the solution to give between 0.25 mg and 2.0 mg protein per 1 mL of suspension, as required. Vesicle suspension was then frozen and thawed three times. Subsequently, the formulation was passed through a micro-porous filter (200 nm; Poretics, CA) under pressure. To check the reproducibility of vesicle manufacturing, the optical density at 400 nm was measured with each preparation and confirmed to be approximately constant.

By varying surfactant-to-lipid ratio the vesicular aggregate deformability was controlled, up to the concentration at which membranes became unstable, owing to the high surfactant concentration, and reverted into a micellar form. Lipid vesicles without the surfactant added, which are commonly known as liposomes and have at least 10× less flexible membranes than Transfersomes, were used as negative controls.

Total lipid concentration was typically 10 w-%, unless stated otherwise. Antigen concentration was typically, but not necessarily, of the order of 1 mg/mL. A buffer containing microbicide provided the bulk phase. For other suitable compositions the expert is explicitly referred to other publications and patents from our laboratory.

Immunizations were done with different formulations, including the ultradeformable vesicles without antigens; such vesicles then contained the tetanus toxoid (with or without lipid A) and free immunogen. Each formulation was tested on six mice, unless stated otherwise.

In the case of subcutaneous immunization, 40 μg of immunogen was injected per mouse. For a non-invasive administration, tetanus toxoid doses between 1 μg and 80 μg, associated with different carriers, were administered per mouse on the intact skin of upper dorsum. All non-injected formulations were applied with a high precision pipette and left to dry; during this period mice were kept in separate cages to minimize the applied material abrasion, such as might result from the rubbing of the murine backs on each other. Animals were boosted every two weeks, that is on days 14 and 28; the total immunization scheme thus consisted of three doses, and comprised a prime and two boosts.

Animals were bled retro-orbitally on the days 7, 21 and 35. The collected blood was first allowed to clot. After a brief centrifugation in a micro-centrifuge the serum was separated, de-complemented at 56° C. for 30 min, and then stored at −20° C., until the total antibody concentration and the specific antibody isotypes was determined.

Absorbency measurements were done using standard UV-vis spectrometer.

Measurement of tetanus toxoid (TT) specific antibodies in serum by ELISA. The level of anti-tetanus antibodies was determined by ELISA in the customary fashion, typically in a duplicate. In brief, ELISA plates (maxisorp: NUNC, Germany) were coated with an aliquot (100 μL containing 10 μg of TT/mL) in coating buffer ($Na_2CO_3$/$NaHCO_3$, pH=9.6) for 3 hours at 37° C. Wells were first washed thrice with 200 μL/well of washing buffer and then blocked with 2% milk in washing fluid (for 1000 mL, 8 g NaCl, 1.45 g $Na_2HPO_4.2H_2O$, 0.2 g $KH_2PO_4$, 0.2 g KCl and 0.05% Tween-20) for 3 hours at 37° C. After single wash with 200 mL/well of washing buffer, the plates were incubated with various dilutions (1/50 to 1/6400) of the test serum. After an overnight incubation at 4° C. the plates were washed thrice with 200 μL/well of washing buffer and incubated with 100 μL of secondary antibody. When determining the amounts of IgG, IgA, or IgM, horse radish peroxidase (hrp) conjugated to the appropriate Anti-Ig was used. After a 3 hours incubation at 37° C., the plates were washed thrice with 200 μL/well of washing buffer and the color was developed using o-phenyl diamine as hrp substrate. 0.4 mg/mL of o-phenyl-diamine in phosphate-citrate buffer (pH 4.5) with 0.4 μL $H_2O_2$ per mL was used for the purpose. After 2 minutes the reaction was stopped by the addition of 50 μL of 2N $H_2SO_4$. The absorbency was measured at 492 nm.

The method used to detect various isotypes was also ELISA based. It relied on the peroxidase-labeled, affinity purified secondary antibodies specific for IgG1 (1:1000), IgG2a (1:1000), IgG2b (1:1000), and IgG3 (1:200) which were all obtained from ICN ImmunoBiologicals. Further secondary antibodies included IgA (1:1000) and IgM (1:1000) linked to horse-radish peroxidase (Sigma, Neu-Ulm, Germany). The correspondingly labeled anti-mouse IgE was purchased from PharMingen (San Diego, Calif. The antigens were again permitted to adsorb on test plates and incubated with the test serum after excess of the antigen had been washed away. Subsequently, 100 μL of appropriate specific secondary antibody solution was added to one of the six different plates, to determine anti-IgG1, IgG2a, IgG2b, IgG3, IgA, IgM, respectively. The plates were incubated for 3 hours at 37° C. and processed further as described in previous paragraphs.

Challenge with antigen (the tetanus toxin) in vivo. On the day 35, test animals were challenged by injecting 50 times the $LD_{50}$ of the tetanus toxin subcutaneously (s.c.). (The actual value of $LD_{50}$ was fixed in separate experiments, during which a group of 16 weight-matched animals was challenged s.c. with increasing amounts of toxin and the number of survivors was determined.) To determine the acute TT toxicity in vaccinated animals, the clinical status of such test mice was recorded for 4 days after the first challenge.

Non-protected mice showed signs of paralysis after 24 hours resulting in death, after 36 hours, at latest. Animals which developed no symptoms of paralysis or other anomaly over a 4 days period following the challenge were deemed immune against tetanus.

The long-term immunity was tested by challenging all immunized mice on a monthly basis with a dose of toxin corresponding to 50 times $LD_{50}$, for at least half a year.

EXAMPLES 1-2

Aggregate Size (Stability) Effect

Highly Deformable Vesicles (Transfersomes™: IDEA):
 87.4 mg phosphatidylcholine from soy bean (SPC)
 12.6 mg sodium cholate (NaChol)
 0.04 mol-% monophosphoryl Lipid A (MLA, LA) relative to SPC
 0.9 mL phosphate buffer, 10 mM, pH 6.5
 0.1 mL ethanol (Mixed Lipid) Micelles:
 65 mg phosphatidylcholine from soy bean (SPC)
 35 mg sodium cholate (NaChol)
 0.04 mol-% monophosphoryl Lipid A (MLA) relative to SPC
 0.9 mL phosphate buffer, 10 mM, pH 6.5
 0.1 mL ethanol Tetanus TOXOID (2 mg/mL; Accurate Antibodies) used at the dose of 40 µg (20 µL) or 80 µg (40 µL) TT per mouse and immunization Application area: 1 cm² or 2 cm² for 40 µg or 80 µg TT per mouse on the upper dorsum.

To test the effect of formulation stability on the immunological properties of various, epicutaneously administered formulations, two kind of aggregates were prepared: relatively large vesicles (diameter between 100 nm and 200 nm) and relatively small micelles (diameter below 50 nm). The latter were chosen in the expectation that under suboptimal conditions (owing to the lipid degradation or inappropriate aggregate composition) the latter may arise from the former.

Antibody titres, as reflected in the serum absorbency at 492 nm, are shown in FIG. 1. They show that mixed lipid micelles are less efficient antigen carriers than ultradeformable mixed lipid vesicles (Tfs) loaded with the same amount of TT. Mixed micelles containing less potent detergents (with lesser skin permeation enhancing capability) were even less efficient immune response mediators.

Animal protection data reveal a similar trend, as is seen in lower panel of FIG. 1.

EXAMPLES 3-4

Aggregate Deformability Effect

Conventional Lipid Vesicles (Liposomes):
 100 mg phosphatidylcholine from soy bean (SPC)
 0.4 mol-% monophosphoryl Lipid A (MLA) relative to SPC
 0.5 mL phosphate buffer, 10 mM, pH 6.5
 2 mg/mL tetanus toxoid (Accurate Antibodies)

Highly Deformable Vesicles (Transfersomes™):
 87.4 mg phosphatidylcholine from soy bean (SPC)
 12.6 mg sodium cholate (NaChol)
 0.04 mol-% monophosphoryl Lipid A (MLA) relative to SPC
 0.9 mL phosphate buffer, 10 mM, pH 6.5
 0.1 mL ethanol Tetanus toxoid used at the dose of 40 µg or 80 µg TT/mouse/immunization Application area: 1 cm² or 2 cm² for 40 µg or 80 µg TT/mouse/immunization on the upper dorsum.

Results obtained with the conventional vesicles differ from the data measured with highly deformable vesicles: simple liposomes, which do not cross the narrow pores in a barrier also do not elicit a substantial antibody titre. Conversely, the vesicles with a highly flexible and deformable, and thus better adaptable, membrane which were shown separately to move through the narrow pores in a barrier with greater ease, generate an appreciable quantity of antibody when applied on intact skin, according to the results of serum absorbency measurements (cf. FIG. 2).

EXAMPLES 5-10

Antigen Dose Effect

Highly Deformable Vesicles:
 86.3 mg phosphatidylcholine from soy bean (SPC)
 13.7 mg sodium cholate (NaChol)
 0.04 mol-% monophosphoryl Lipid A (MLA) relative to SPC
 0.9 mL phosphate buffer, 10 mM, pH 6.5
 0.1 mL ethanol Tetanus Toxoid (TT: Accurate Antibodies, New York, USA) Concentration:
 empty, 0.25 mg/mL, 0.5 mg/mL, 1 mg/mL, 2 mg/mL, giving raise to 0 µg, 10 µg, 20 µg, 40 µg or 80 µg TT/mouse/immunization Application area: 1 cm² for 0 µg, 10 µg, 20 µg, 40 µg and 2 cm² for 80 µg TT/mouse/immunization on the upper dorsum.

The results of this experimental series are illustrated in FIG. 3. It clearly shows the increase in immune response to epicutaneously administered tetanus toxoid in ultradeformable carriers with increasing TT dose. This is reflected in serum absorbency (up to the dose of 20 µg/immunization), in specific antibody titre (up to the dose of 40 µg/immunization), and in the survival data (which do not saturate for doses up to 80 µg/immunization).

Less clarity is found in isotype distribution pattern, except for IgG1 (with a strong indication for the response saturation) and for IgG2b (perhaps, with the saturation between 40 µg and 80 µg per immunization). IgM shows dose dependence similar to that of IgG1. The picture obtained for IgG2a is confusing.

EXAMPLES 11-13

Antigen Purity Effect

Highly Deformable Vesicles:
 as described with examples 5-10 (except in that the group treated with impure TT did not receive immunoadjuvant lipid A)

Tetanus toxoid: 2 mg/mL, corresponding to 80 µg TT per mouse/immunization

Application area: 2 cm² on the upper dorsum.

Antigen purity strongly affects the level of murine protection against tetanus toxin when the toxoid has been applied non-invasively on the skin. (Similar results obtained with injected antigen are not shown).

To substantiate the above mentioned statement, the medium filtrate from a culture of *Clostridium tetani* grown in vitro first was used as an impure antigen. To obtain partially purified antigen, such filtrate was passed through a 10 kDa cut-off membrane and washed thoroughly with phosphate buffer, pH 6.5; in the process, the culture filtrate was concentrated 15 times. Purified toxoid was purchased from Accurate Antibodies, NY, USA.

Swiss albino mice (n=6) were immunized with identical nominal dose of impure antigen, with partially purified antigen supplemented with monophosphoryl lipid A or with purified antigen with monophosphoryl lipid A added. The antigen was always associated with similar Transfersomes. The composition and the method of preparation for the latter were the same are as described with previous examples. The details of immunization schedule, bleeding times and challenge as well as analysis details were also similar to those mentioned before.

The results are given in FIG. 4. They demonstrate the role antigen purity plays in determining the quality as well as the strength of an immune response against TT. The data shown in FIG. 4, moreover, indicate that the absorbency of even the specific antibody titre is not a reliable predictor of the therapeutic, that is, of prophylactic effect of an epicutaneous vaccination. This is due to the big differences in specific antibody isotypes which only contain a substantial proportion of Th1-like IgG2b compared to Th2-like IgG1 component if sufficiently pure antigen is used (see also page 12).

EXAMPLES 14-15

Comparison of Epicutaneous and Subcutaneous Administration

Highly Deformable Vesicles, Transfersomes™ (IDEA):
 as described with examples 5-10

Tetanus Toxoid Dose:
- 80 μg TT per epicutaneous immunization (using 2 mg TT/mL and application area of 2 $cm^2$)
- 40 μg TT per subcutaneous injection (using 2 mg TT/mL)

Using the same experimental procedures as described with examples 1-4, as appropriate, the antibody-specific serum titre, the level of animal protection against tetanus toxin and relative occurrence of different specific antibody isotypes was determined.

The results are given in FIG. 5. While the immunization dependent increase in serum absorbency is comparable after invasive and non-invasive antigen administration the titre in the latter case is somewhat lower by the factor of 6 after primary immunization and by the factor of 8 after second boost. Likewise, while the TT-specific levels of Th2-indicating IgG1 are similar in both arms of this experiment, the specific readings for other antibody subtypes, especially for IgG2a and at early time points also for IgG2b are by the factor 25 and 3, respectively, higher after antigen injections. However, the likelihood for the test mice to survive a subsequent challenge with a normally lethal dose of injected tetanus toxin is independent of the route of antigen administration, within the framework of this experimental series at least.

EXAMPLES 16-17

Adjuvant Skin Treatment (Pre-Injection) Effect

Highly Deformable Vesicles, Transfersomes™ (IDEA):
- 89.3 mg phosphatidylcholine from soy bean (SFC)
- 10.7 mg sodium cholate (NaChol)
- 0.04 mol-% monophosphoryl Lipid A (MLA) relative to SPC
- 0.9 mL phosphate buffer, 10 mM, pH 6.5
- 0.1 mL ethanol Tetanus toxoid, 2 mg/mL, corresponding to 80 μg TT per mouse/immunization of 6 Swiss albino mice per group using impure antigen Application area: 2 $cm^2$ on the upper dorsum.

Transcutaneous transport of macromolecules associated with Transfersomes across the skin seems to be extremely gentle; it therefore fails to trigger the immune system toward Th2-like immune response, if the antigen is used in a low amount or is impure. To change the situation, the skin can be (pre)stimulated to release corresponding messenger molecules from the organ prior to the actual non-invasive antigen administration by means of ultradeformable vesicles. For this purpose we have pre-injected the application site with 0.1 mL of saline, or a mild formulation of non-antigenic vesicles, prepared from biodegradable material of similar composition as the antigen carrying vesicles one day before using the latter. For additional control, incomplete Freund's adjuvant was also injected in different animals 24 hours before the application of immuno-carriers on the skin.

Illustrative examples of results are given in FIG. 6. They reveal higher specific antibody titres, especially for and improved protection in the mice that were pre-treated by injections rather than carrier formulation on the skin, which served as a control. The effect of incomplete Freund's adjuvant is surprisingly weak.

It is noteworthy that the serum absorbency or the specific antibody titre and animal survival, that is protective vaccination effect, are not correlated.

EXAMPLES 18-21

Low Molecular Weight Adjuvant (Lipid A) Effect

Highly Deformable Immuno-Modulated TT-Transfersomes™ (IDEA):
- 86.3 mg phosphatidylcholine from soy bean (SPC)
- 13.7 mg sodium cholate (NaChol)
- 0.04 mol-% monophosphoryl Lipid A (LA) relative to SPC
- 0.9 mL phosphate buffer, 10 mM, pH 6.5
- 0.1 mL ethanol Highly deformable standard immuno-vesicles, TT-Transfersomes™ (IDEA): as above but without LA added Tetanus toxoid: 2 mg/mL, with 20 μL or 40 μL corresponding to 40 μg or 80 μg TT per immunization Application area: 1 $cm^2$ or 2 $cm^2$, respectively, on the upper dorsum.

We believe that immuno-active, typically immunopotentiating, molecules must be present in the skin at the time of antigen presentation to the body by TT carriers that have crossed the barrier in order to achieve the desired immunological action of the antigen. To substantiate this conclusion we compared the outcome of non-invasive immunopresentation of TT by means of Transfersomes with or without a well known immunostimulant, monophosphoryl lipid A (LA), which is known to elicit generation of TNF in the body, for example. Two different antigen doses were used. In either case substantial titres and a measurable prophylactic immune response (partial immunity) was reached.

The absorbency of the serum increases as one would expect (cf. FIG. 7). Conversely, the effect of LA is better seen for the lower than for the higher dose used. This may be due to experimental variability or else reflect non-linearity of dose vs. action curve for the typical immunization data. It is possible, for example, that adjuvant is only efficient in the low dose range, whereas in the high dose regiment the system is quasi-saturated, leaving little possibility for the adjuvant to further enhance the immune response within the scope of experimental set-up. Complete animal protection against a normally lethal challenge with 50 $LD_{50}$ was achieved in this test series with the higher TT dose in combination with LA only.

It was further observed that Th1-cytokine IgG2b was higher with LA groups, compared with the groups that received no LA. This difference was more pronounced for low doses, by the factor of 4, than for high doses, where only an enhancement by the factor of 2 was observed. Th2-cytokine IgG1 was present predominantly, except in the low dose with LA group in which IgG2b contributed comparably.

EXAMPLES 22-23

High Molecular Weight Adjuvant

IL-12 Cytokine Effect

Highly Deformable Vesicles, Transfersomes™ (IDEA):
    as described with examples 5-10, plus
    0.01 mg IL-12 per mL immunogen suspension Tetanus toxoid, 2 mg/mL, corresponding to 80 μg TT per mouse/immunization (partially purified as described with examples 9-11)

Application area: 2 cm² on the upper dorsum of Swiss albino mice.

To study the effect of cytokines on results of non-invasive, epicutaneous vaccination with tetanus toxoid, a combination of monophosphoryl lipid A with 0.4 μg IL-12 per mouse was used. 80 μg of IL-12 was administered per mouse in association with Transfersomes loaded with tetanus toxoid and monophosphoryl lipid A. The details of immunization schedule, bleeding intervals, or the final challenge with the tetanus toxin were the same as mentioned above.

The results of experimental series are illustrated in FIG. 8. The corroborate the conclusion that the presence of pro Th2 cytokines in the skin during the course of immunopresentation following an epicutaneous TT administration positively affects the outcome of vaccination. This is seen in serum absorbency, the specific antibody titre as well as in the test animal survival probability.

The effect discussed with examples 22-23 was verified by incorporating cytokines other than IL-12 into immunogen formulation. The results are shown in FIG. 9.

EXAMPLES 24-25

High Molecular Weight Adjuvant (IFN-γ and GM-CSF+IL-4) Effect

Highly Deformable Vesicles, Transfersomes™ (IDEA):
    as described with examples 5-8, plus
    0.05 mg IFN-γ and 0.004 mg GM-CSF and 0.004 mg IL-4 per mL
    immunogen suspension Tetanus toxoid. 2 mg/mL, corresponding to 80 μg TT per mouse/immunization (impure)

Application area: 2 cm² on the upper dorsum of Swiss albino mice.

The effect discussed with examples 22-23 was confirmed also with a blend of different cytokines.

EXAMPLES 28-29

Booster Effect

Maturation of Immune Response

In most of previous examples, a consistent pattern was observed whenever the absorbency was measured during the time course of immunization. The immune response increased with each boost, compared to the response obtained after primary immunization (see FIGS. 3, 4, 5, 6, 7, 8). The primary response was characterized by predominance of IgM, followed by gradual appearance of IgG after the first boost and by the appearance of even greater amounts of IgG after the second boost, with a concurrent disappearance of IgM. This typical pattern of isotype signifies affinity maturation in the immune response. During the process, the average affinity of a mixture of specific antibodies increases with repeated immunizations.

Results of various epicutaneous vaccination experiments suggest that it may be advantageous to combine an invasive priming vaccination with non-invasive secondary (boost) immunization.

EXAMPLES 30-72

Release of Cytokines from the Skin In Vitro by Transfersomes

Highly Deformable Vesicles (Transfersomes Type C):
    87.4 mg phosphatidylcholine from soy bean (SPC)
    12.6 mg sodium cholate (NaChol)
    0.9 mL phosphate buffer, 50 mM, pH 7.3
    2.5 μL thereof.

Highly Deformable Vesicles (Transfersomes Type T):
    50 mg phosphatidylcholine from soy bean (SPC)
    50 mg polysorbate (Tween 80)
    0.9 mL phosphate buffer, 50 mM, pH 6.5
    2.5 μL thereof.

Positive Control A:
    2.5 μL 5% sodium dodecylsulphate (SDS)

Positive Control B:
    100 μL lipopolysaccharide (LPS; $10^5$ U/mL)

Negative Control:
    2.5 μL of phosphate buffered saline (PBS)
    All products were tested undiluted.

Cell type: Normal human keratinocytes, forming a pluristratified epithelium with a compact stratum corneum were used; histology revealed strong resemblance with human epidermis in vivo.

Method: Keratinocytes were inoculated on polycarbonate filter inserts of 0.63 cm² in chemically defined, supplemented medium, and cultured for 17 days at the air-liquid interface.

Test measurements: given amount of each tested product was deposited with a micropipette and spread evenly over the surface of the stratum corneum of eight reconstituted epidermis using a small sterile device. The cultures were incubated at 37° C. 5% $CO_2$ for 24 hours. Quadruplicate cultures (except for the LPS treated cells which were incubated in duplicate) were washed with 0.5 mL of PBS and incubated on 300 µL of 0.5 mg/mL MTT for 3 hours at 37° C., 5% $CO_2$.

The release of inflammatory mediators (IL1α, IL2, IL4, IL8, IL10, IFN-γ, and TNF-α) in the medium underlying the tissues was quantified using ELISA kits (R&D systems UK; Quantikine), specific for each type of immuno-modulator to be measured.

|  | IL1-α (pg/mL) Mean +/− SD | IL8 (pg/mL) Mean +/− SD | TNF-α (pg/mL) |
|---|---|---|---|
| Negative control (PBS, n = 2) | 5.1 +/− 0.5 | <31 | not detectable |
| Positive control A (SDS 5%, n = 2) | 314.2 +/− 6.1 | 147.5 +/− 32 | not detectable |
| Positive control B (LPS, n = 1) | 32.0 | 5161 | 113.4 |
| Transfersomes C (02-05, n = 2) | 12.3 +/− 0.9 | 68.3 +/− 16.8 | not detectable |
| Transfersomes T (TT0009/175, n = 2) | 11.7 +/− 1.2 | 50.8 +/− 14.0 | not detectable |
| Transfersomes O (TT0017/15, n = 2) | 185.5 +/− 170.1 | 58.4 +/− 27.0 | not detectable |

The relatively big standard deviation observed with Transfersomes O can be explained by the fact that the product was difficult to spread uniformly onto the stratum corneum of the reconstructed epidermis.

TNF-α level was increased to the level of 113.43 pg/mL when the cells were in contact with the positive controls containing LPS, which is an established immunoadjuvant.

IL8 concentration after cells incubation with Transfersomes exceeded the lower limit of detection by just the factor of 2, which in one case is not and in the other is barely significant at 95% confidence level, but in either situation is negligible compared to the increase observed with the positive control containing the immunoadjuvant LPS, which gave a 167× higher value.

Non-specific irritant, SDS, released a great quantity of IL-1α from the skin cells into the bathing medium in vitro. The possibility exists, that an amount of comparable quantity was released from the cells incubated with Transfersomes O, comprising the potentially irritating oleic acid at a high concentration, but firm conclusion is prevented by the great standard deviation in the results obtained with the latter test system.

IL-1α concentration for the other tested Transfersomes of type A and type B changed to approximately 2 times the background level. This difference is statistically significant, compared to negative controls, but practically negligible, taken that the increase observed with the positive control containing LPS was more than 60 times higher.

IFN-γ, IL-2, IL4 or IL10 was not elevated to a measurable level, suggesting a lack of release of these cytokines, under any other test condition.

Taken together the above mentioned findings suggest that Transfersomes do not release cytokines or induce the generation of such molecules from the skin cells. This explains the need for using immunoadjuvants/modulators when antigens or allergens are to be delivered across the skin with such carriers and elicit a therapeutic or prophylactic immune response.

EXAMPLES 73-82

Bacterial Wall Component, Cholera Toxin, as Specific Immuno-Adjuvant

Highly Deformable Vesicles, Transfersomes™:
  86.3 mg phosphatidylcholine from soy bean (SPC)
  13.7 mg sodium cholate (NaChol)

0.9 mL phosphate buffer, 10 mM, pH 6.5

Cholera toxin (CT; Sigma, Neu-Ulm), 10 μg/immunization plus, if required,

Tetanus toxoid (TT, pure; Accurate Antibodies) 2 mg/mL,

Volume doses corresponding to 0 μg TT/mouse/immunization (negative control), 1 μg TT/mouse, 5 μg TT/mouse, 10 μg TT/mouse, 20 μg TT/mouse, 40 μg TT/mouse (in the case of CT usage) and 80 μg TT/mouse (without CT) were used epicutaneously over an area of up to 2 $cm^2$ on the upper dorsum of 4-6 Swiss albino mice; 20 μg TT/mouse/immunization were injected subcutaneously at the corresponding site in the positive control group. Unimmunized mice were used as another negative control.

The protective effect of epicutaneous antigen administration was excellent when cholera toxin was included into the test formulation in combination with the tetanus toxoid. Formulation without this immunoadjuvant yielded inferior protection, as demonstrated by the fact that 1 animal out of 4 (25%) was paralytic after the challenge with tetanus toxin.

The results shown in FIG. 10 reveal that the antigen doses in excess of 20 μg/immunization ensured complete protection, which was not the case with the other tested adjuvants or adjuvant treatments (see previous examples). Lower dosage of antigen gave qualitatively similar effect but was insufficient to guarantee the survival of all test mice, except in the test group which received 5 μg TT/immunization. (This implies that TT doses between 1 μg/immunization and 15 μg/immunization belong to the transition region.) Other doses of cholera toxin might be equally or even more beneficial, however.

EXAMPLES 83-85

Heat Labile Toxin (HLT) from *E. coli* has as an Immuno-Adjuvant

Highly Deformable Vesicles, Transfersomes™:

86.3 mg phosphatidylcholine from soy bean (SPC)

13.7 mg sodium cholate (NaChol)

0.9 mL phosphate buffer, 10 mM, pH 6.5

Heat Labile Toxin (HLT, SIGMA, Neu-Ulm), 1 mg/mL plus, if required

Tetanus Toxoid (TT, pure, Accurate Antibodies) 2 mg/mL

Various relative adjuvant/antigen concentrations were used to test the effect of one of most commonly used ADP ribosylating enzymes for transcutaneous vaccination. Transfersomes were prepared as described in previous examples. Other experimental details (animal housing; antigen administration; titre determination) are described hereinabove.

Volume doses corresponding to 20 μg TT/mouse/e.c. immunization and 1 to 2 μg HLT/mouse/e.c. immunization and a positive control with 0.5 µg TT for s.c. injection were used to immunize Swiss albino mice. The results are illustrated in FIG. 11.

Anti-TT titres were found to increase when HLT was used as an adjuvant free s.c. injection of antigen or compared to an adjuvant free administration of TT in transfersomes on the skin. Humoral response and the protection against a normally lethal challenge with Tetanus Toxin were found to be dose dependent, with the higher anti-TT titres and improved survival for the higher dose of HLT. The measured results (data not shown) suggest that useful HLT dosage starts in the range 100 ng/dose while the highest practically useful dose under experimental conditions used in this test series is approx. 100-times greater. This reveals that the upper limit for adjuvant dose that should be used in conjunction with epicutaneously administered Transfersomes is of comparable order of magnitude as, and at most should be 10× higher than, that employed in conventional invasive (s.c.) immunizations; the lower practical limit, in our opinion, is 1-2 orders of magnitude smaller than the typical s.c. dose. It is proposed that similar relationships will also hold for other related immuno-adjuvants.

EXAMPLES 86-87

Local Pre-Treatment with Histamine

Highly Deformable Vesicles, Transfersomes™:
 86.3 mg phosphatidylcholine from soy bean (SPC)
 13.7 mg sodium cholate (NaChol)
 0.9 mL phosphate buffer, 10 mM, pH 6.5
 Tetanus Toxoid (TT, pure, Accurate Antibodies) 2 mg/mL 1 mg/ml histamine solution in phosphate buffer, 10 mM, pH 6.5

In order to test the effect of alternative means for immune-response modulation, mice were injected with 10 µg histamine in solution at the site of e.c immunization immediately or 15 minute prior to the antigen administration on the skin in Transfersomes. The expectation was that this would induce cytokine release from the skin, and/or have some other positive effect on the outcome of non-invasive transcutaneous immunization. In order to test this hypothesis, Transfersomes were prepared as described in the previously described examples and were carried out with Swiss albino mice as described herein above (except the pre-treatment with histamine).

FIG. 12 confirms the above mentioned working hypothesis. The results reveal good humoral response and the requirement for a time period between histamine injection and e.c. immunization to achieve reasonable protection against a challenge with Tetanus Toxin. Comparison with the results measured with TT in Transfersomes on the skin without an adjuvant thus shows that histamine injection is helpful for boosting animal immune response.

EXAMPLES 88-89

Different Administration Routes for Primary and Boost Immunization

Highly Deformable Vesicles, Transfersomes™:
 86.3 mg phosphatidylcholine from soy bean (SPC)
 13.7 mg sodium cholate (NaChol)
 0.9 mL phosphate buffer, 10 mM, pH 6.5
 Cholera Toxin (CT, SIGMA, Neu-Ulm), 0-1 µg/immunisation
 Tetanus Toxoid (TT, pure, Accurate Antibodies) 2 mg/mL A detailed description of vesicle preparation and animal experimentation can be found in previous examples hereinabove.

Volume doses corresponding to 20 µg TT alone or to 0.5 µg TT plus 1 µg CT were injected s.c. for primary immunization but were applied epicutaneously for booster immunization. This combination increased the efficacy of vaccination substantially, as implied earlier.

Anti-TT titres were high enough to yield 100% protection against a challenge with Tetanus Toxin (FIG. 13). Comparison with the data from previous examples carried out with adjuvant free TT-Tfs on skin clearly demonstrate the usefulness of combined s.c./e.c. vaccination protocol.

The data therefore suggest that antigen-loaded Transfersome™ applied on the skin provide an attractive complement to invasive antigen administration, which should be particularly important for the purpose of booster immunization.

EXAMPLE 90

Bi-Valent Vaccination with Tetanus Toxoid and Cholera Toxin as Antigens

Highly Deformable Vesicles, Transfersomes™:
 86.3 mg phosphatidylcholine from soy bean (SPC)
 13.7 mg sodium cholate (NaChol)
 0.9 mL phosphate buffer, 10 mM, pH 6.5
 Cholera Toxin (CT, SIGMA, Neu-Ulm), 10 µg/immunization
 Tetanus Toxoid (TT, pure, Accurate Antibodies) 2 mg/mL Cholera Toxin not only works as an adjuvant to improve anti-TT response (see previous examples), but is also an antigen by itself. The adjuvant, consequently, can play the role of a secondary antigen, when used at certain concentration. The adjuvancy and immunogenicity are not linearly correlated, however, which offers interesting possibilities for optimizing the outcome of vaccination outcome (also with regard to side effects and allergy induction.) Working with CT in Transfersomes tested in mice, we found out that CT doses between less than 50 ng and at least 10 µg per application are useful for the purposes described in this application.

Anti-cholera toxin antibodies in the mice that were treated with different volumes of test formulation on the skin (corresponding to 10 µg TT and 10 µg CT) are indicative of CT antigenicity. This corroborates the potential of ultradeformable vesicles for making at least bi-valent vaccines based on Transfersomes™ containing more than one antigen.

FIG. 14 shows TT and CT titres measured with the mice that were previously immunized with TT and CT in the same carrier.

LITERATURE

Cevc, G. Drug delivery across the skin. Exp. Opin. Invest. Drugs (1997) 6: 1887-1937.
Cevc, G., Gebauer, D., Schätzlein, A. Blume, G. Ultraflexible Vesicles, Transfersomes, Have an Extremely Low Permeation Resistance and Transport Therapeutic Amounts of Insulin Across the Intact Mammalian Skin. Biochim. Biophys. Acta (1998) 1368: 201-215.
Deng, H., Qun, L., Khavari, P. A. Sustainable cutaneous gene delivery. Nature Biotechnology (1997) 15: 1388-1390.

Fries, K. M., Blieden, T., Looney, R. J., Sempowski, G. D., Silvera, M. R., Willis, R. A., Phipps, R. P. Evidence of fibroblast heterogeneity and the role of fibroblast subpopulations in fibrosis. Clin. Immunol. Immunopathol. (1994) 72: 283-292.

Glenn, G. M., Rao, M. Matyas, G. R., Alving, C. R. Skin immunisation made possible by Cholera toxin. Nature (1998a) 851: 391.

Glenn, G. M., Scharton-Karsten T, Vasell R, Mallet C. P., Hale T. L. and Alving C. R. Transcutaneous Immunization with Cholera toxin Protects Mice Against Lethal Mucosal Toxin Challenge. J. Immunol. (1998b) 161: 3211-3214.

Kondo, S., Sauder, D. N. Epidermal cytokines in allergic contact dermatitis. J. Am. Acad. Dermatol. (1995) 33: 786-800.

Lohoff, M., Gessner, M., Bogdan, C., Roellinghoff, M. The Th1/Th2 paradigm and experimental murine Leishmaniasis. Int. Arch Allergy Immunol. (1998) 115: 191-202.

Luger, T. A., Schwarz, T. The role of cytokines and neuroendocrine hormones in cutaneous immunity and inflammation. Allergy (1995) 50: 292-302.

Nasir, A., Gaspari, A. A. Contact dermatitis. Clinical perspectives and basic mechanisms. Clin. Rev. Allergy and Immunol. (1996) 14: 151-184.

Pastore, S., Fanales-Belaso, E., Abbanesi, C., Chinni, L. M., Giannetti, A., Girolomoni, G. Granulocyte macrophage colony stimulating factor is overproduced by keratinocytes in atopic dermatitis: Implications for sustained dendritic cell activation in the skin. J. Clin. Invest. (1997) 99: 3009-3017.

Paul, A., Cevc, G. Non-invasive administration of protein antigens. Epicutaneous immunisation with the bovine serum albumin. Vaccine Res. (1995) 4: 145-164.

Paul, A., Cevc, G., Bachhawat, B. K. Transdermal immunisation with large proteins by means of ultradeformable drug carriers. Eur. J. Immunol. (1995) 25: 3521-3524.

Paul, A., Cevc, G., Bachhawat, B. K. Transdermal immunisation with an integral membrane component, gap junction protein, by means of ultradeformable drug carriers, Transfersomes. Vaccine (1997) 16: 188-195.

Schätzlein, A., Cevc, G. Non-uniform cellular packing of the stratum corneum and permeability barrier function of intact skin: a high-resolution confocal laser scanning microscopy study using highly deformable vesicles (Transfersomes). Br. J. Dermatol. (1998) 138: 583-592.

Strange, P., Skov, L. Lisby, S., Nielsen, P. L., Baadsgard, O. Staphylococcal enterotoxin B applied on intact normal and intact atopic skin induces dermatoma. Arch. Dermatol. (1996) 132: 27-33.

Wang, L.-F., Lin, J.-Y., Hsieh, K.-H., Lin, R.-H. Epicutaneous exposure of protein antigen induces a predominant Th2-like response with IgE production in mice. J. Immunol. (1996) 156: 4079-4082.

The invention claimed is:

1. A transdermal antigenic composition, comprising at least 4 components, which are:
   (a) a transdermal carrier comprising a penetrant suspended or dispersed in an aqueous solvent,
      the penetrant being in the form of a minute fluid droplet surrounded by a coating of one or more layers of at least 2 substances that differ by at least a factor of 10 in solubility,
      the substances forming homoaggregates of one substance and/or heteroaggregates of the at least 2 substances, the average diameter of homoaggregates of the more soluble substance, or the average diameter of the heteroaggregates of the at least 2 substances, being smaller than the average diameter of homoaggregates of the less soluble substance, and/or the more soluble substance solubilizing the droplet and the content of the more soluble substance being up to 99 mol-% of the concentration required to solubilize the droplet or corresponding to up to 99 mol-% of the saturating concentration in an unsolubilized droplet, whichever is higher, and/or wherein the elastic deformation energy of the droplet surrounded by the coating is at least 5 times lower than the elastic deformation energy of red blood cells or of a phospholipid bilayer having fluid aliphatic chains;

(b) a compound which specifically has or induces cytokine or anti-cytokine activity;

(c) an antigen or mixture of different antigens and/or an allergen or mixture of different allergens; and (d) a chemical irritant.

2. The antigenic composition of claim 1, wherein the at least two substances are two ionization states or salt forms of the same substance.

3. The antigenic composition according to claim 1, wherein the less soluble substance with the tendency to aggregate is a polar lipid, and the more soluble substance is a surfactant.

4. The antigenic composition according to claim 1, wherein the average diameter of the penetrant is between 30 nm and 500 nm.

5. The antigenic composition according to claim 1, wherein the total weight of droplets in the antigenic composition for use on human or animal skin is 0.01 weight-% (w-%) to 40 w-% of total mass of the antigenic composition.

6. The antigenic composition according to claim 1, wherein the total antigen concentration is between 0.001 and 40 w-% of the total penetrant mass.

7. The antigenic composition according to claim 1, wherein the compound is IL-4, IL-3, IL-2, TGF, IL-6, IL-7, TNF, IL-1a and/or IL-1b, IL-12, IFN-g, TNF-b, IL-5, IL-10, a type I interferon, IFN-alpha, or IFN-b.

8. The antigenic composition according to claim 1, wherein the compound is an anti-cytokine antibody or an active fragment thereof.

9. The antigenic composition according to claim 1, wherein the antigen is from a pathogen.

10. The antigenic composition according to claim 9 wherein said pathogen is selected from the group consisting of extracellular bacteria, gram-negative bacteria, gram-positive bacteria, bacteria and viruses, which survive and replicate within host cells, fungi prospering inside host cells, parasites, the causative agent for cholera, *Haemophilus* species, pathogens triggering paratyphoid, pathogens triggering plague, pathogens triggering rabies, *Clostridium tetani*, pathogens triggering rubella, and pathogens that cause various neoplasiae, auto-immune diseases or are related to other pathological states of the animal or human body which do not necessarily result from pathogen infections.

11. The antigenic composition according to claim 1, wherein the allergen is of xenogenic or endogenic origin; from a microorganism, an animal or a plant; a man made and/or irritating inorganic substance; or a part or component of the human body which was incorrectly processed by or exposed to the body immune system.

12. The antigenic composition according to claim 1, wherein the concentration of the compound used is up to 1000 times higher than a concentration optimum established in corresponding tests performed by injecting the antigenic compositions or performing the tests in vitro.

13. The antigenic composition according to claim 1, wherein the irritant is selected from the classes of allergenic metal ions, acids, bases, irritating fluids, (fatty-) alcohols, (fatty-) amines, (fatty-) ethers, (fatty-) sulphonates, or -phosphates or combinations thereof.

14. The antigenic composition according to claim 1, wherein the irritant is a solvent or amphiphile or combination thereof.

15. The antigenic composition according to claim 1, wherein the irritant is selected from the group consisting of surfactants and combinations thereof.

16. The antigenic composition according to claim 15 wherein the surfactant enhances skin permeation.

17. The antigenic composition according to claim 1, wherein the concentration of the irritant is below by at least a factor of 2 to a factor of 10 or more a concentration which is unacceptable owing to local irritation in tests on the same or a comparable subject.

18. The antigenic composition according to claim 1, wherein the allergen is an inhalation allergen, food allergen, drug allergen, contact allergen, injection allergen, invasion allergen, or depot allergen.

19. The antigenic composition according to claim 1, wherein the applied dose of the antigen differs by the factor of 0.1 to 100 from the dose which would have to be used with an injection.

20. The antigenic composition according to claim 1, wherein the applied dose of an antigen is less than 10 times higher than the dose which would have to be used with an injection.

21. The antigenic composition according to claim 1, wherein the applied penetrant dose is between 0.1 mg/cm$^2$ and 15 mg/cm$^2$.

22. The antigenic composition according to claim 1, wherein the antigen is a pure or purified antigen.

23. A kit, comprising at least one dose of the antigenic composition according to claim 1 in packaged form.

24. A method for generating a protective immune response in a mammal comprising the step of administering to the mammal an antigenic composition according to claim 1.

25. The method according to claim 24, wherein a suspension of antigen-free penetrants is loaded with the antigen to be associated therewith about 30 minutes before administration of the antigenic composition.

26. The method according to claim 24, wherein the antigenic composition is applied on skin after pre-treating the skin by an immunoadjuvant manipulation, the manipulation comprising rubbing, pressing, heating, exposing to an electrical or mechanical field, or injecting a non-immunogenic formulation in the skin, wherein such treatment releases immunoadjuvant compounds from the skin or other peripheral immunoactive tissues or reduces the concentration of antagonists to the desired vaccination and/or the duration of action of said antagonists.

27. The method according to claim 24 wherein immunogen is applied in a non-occlusive patch.

28. The method of claim 24 wherein at least one dose of antigenic composition is administered.

29. The method according to claim 28, wherein the antigenic composition is administered as a booster vaccination.

30. The method according to claim 29, wherein a primary immunization is done invasively and wherein the booster immunization is done non-invasively.

31. The method according to claim 24, wherein the antigenic composition is applied between 2 and 10 times when a non-allergenic antigen is used.

32. The method according to claim 31, wherein the time interval between subsequent administrations is between 2 weeks and 5 years.

33. A method for inducing a protective or tolerogenic immune response comprising administering an antigenic composition, the antigenic composition comprising at least 4 components, which are:
  (a) a transdermal carrier comprising a penetrant suspended or dispersed in an aqueous solvent,
    the penetrant being in the form of a minute fluid droplet surrounded by a coating of one or more layers of at least 2 substances that differ by at least a factor of 10 in solubility,
    the substances forming homoaggregates of one substance and/or heteroaggregates of the at least 2 substances, the average diameter of homoaggregates of the more soluble substance, or the average diameter of the heteroaggregates of the at least 2 substances, being smaller than the average diameter of homoaggregates of the less soluble substance, and/or
    the more soluble substance solubilizing the droplet and the content of the more soluble substance being up to 99 mol-% of the concentration required to solubilize the droplet or corresponding to up to 99 mol-% of the saturating concentration in an unsolubilized droplet, whichever is higher, and/or
  wherein the elastic deformation energy of the droplet surrounded by the coating is at least 5 times lower than the elastic deformation energy of red blood cells or of a phospholipid bilayer having fluid aliphatic chains;
  (b) a compound which specifically has or induces cytokine or anti-cytokine activity;
  (c) an antigen or mixture of different antigens and/or an allergen or mixture of different allergens; and
  (d) a chemical irritant.

34. A transdermal antigenic composition, comprising at least 4 components, which are:
  (a) a transdermal carrier comprising a penetrant suspended or dispersed in an aqueous solvent,
    the penetrant being in the form of a minute fluid droplet surrounded by a coating of one or more layers of at least 2 substances that differ by at least a factor of 10 in solubility,
    the substances forming homoaggregates of one substance and/or heteroaggregates of the at least 2 substances, the average diameter of homoaggregates of the more soluble substance, or the average diameter of the heteroaggregates of the at least 2 substances, being smaller than the average diameter of homoaggregates of the less soluble substance,
    and/or
    the more soluble substance solubilizing the droplet and the content of the more soluble substance being up to 99 mol-% of the concentration required to solubilize the droplet or corresponding to up to 99 mol-% of the saturating concentration in an unsolubilized droplet, whichever is higher, and/or
    wherein the elastic deformation energy of the droplet surrounded by the coating is at least 5 times lower than the elastic deformation energy of red blood cells or of a phospholipid bilayer having fluid aliphatic chains;
  (b) a compound which specifically has or induces cytokine or anti-cytokine activity;
  (c) an antigen or mixture of different antigens and/or an allergen or mixture of different allergens; and
  (d) a chemical irritant;

wherein said (b) and (c) are associated with the penetrant, and wherein said composition is to provide a protective or tolerogenic immune response.

35. The composition of claim 34, wherein (c) comprises a part of a pathogen or an allergen in its natural form or after fragmentation.

36. The composition of claim 34, wherein to provide said protective immune response is to provide complete protection against a normally lethal challenge.

37. The composition of claim 1, wherein said composition is to provide a protective or tolerogenic immune response.

38. The composition of claim 1, wherein said composition is to provide a protective immune response.

39. The composition of claim 34, wherein said composition is to provide a protective immune response.

\* \* \* \* \*